(12) United States Patent
Bantilan et al.

(10) Patent No.: US 11,309,082 B2
(45) Date of Patent: Apr. 19, 2022

(54) SYSTEM AND METHOD FOR MONITORING ENGAGEMENT

(71) Applicant: Groop Internet Platform, Inc., New York, NY (US)

(72) Inventors: Niels Bantilan, Brooklyn, NY (US);
Geoff Gelman, New York, NY (US);
Gil Margolin, Tenafly, NJ (US);
Bonnie K. Ray, Nyack, NY (US);
Andrew Zitek, New York, NY (US)

(73) Assignee: Groop Internet Platform, Inc., New York, NY (US)

( * ) Notice: Subject to any disclaimer, the term of this patent is extended or adjusted under 35 U.S.C. 154(b) by 309 days.

(21) Appl. No.: 16/709,559

(22) Filed: Dec. 10, 2019

(65) Prior Publication Data
US 2020/0185096 A1    Jun. 11, 2020

Related U.S. Application Data

(60) Provisional application No. 62/879,564, filed on Jul. 22, 2019, provisional application No. 62/859,659, (Continued)

(51) Int. Cl.
*G06F 16/00* (2019.01)
*G16H 40/67* (2018.01)
(Continued)

(52) U.S. Cl.
CPC ......... *G16H 40/67* (2018.01); *G06F 16/2282* (2019.01); *G06F 16/24556* (2019.01); *G16H 80/00* (2018.01)

(58) Field of Classification Search
CPC .......... G06F 16/24556; G06F 16/2282; G16H 10/20; G16H 20/70; G16H 50/20
See application file for complete search history.

(56) References Cited

U.S. PATENT DOCUMENTS 6,317,731 B1    11/2001  Luciano
8,346,563 B1    1/2013   Hjelm et al.
(Continued)

FOREIGN PATENT DOCUMENTS

AU    2017101735 A4    1/2018
WO    2018158385 A1    9/2018

OTHER PUBLICATIONS

Calder et al., "An Experimental Study of the Relationship between Online Engagement and Advertising Effectiveness," ScienceDirect, www.sciencedirect.com, Journal of Interactive Marketing, Journal of Interactive Marketing 23 (2009), pp. 321-331. (Year: 2009).*

(Continued)

*Primary Examiner* — Cheryl Lewis
(74) *Attorney, Agent, or Firm* — Stradley Ronan Stevens & Young, LLP

(57) ABSTRACT

Aspects include a computer-implemented method comprising tracking of one or more actions (e.g., patient actions) carried out on a web-based computing platform that enables text, audio, video and/or any other communication between providers and their clients, and aggregating indicators of at least one of these actions into a score calculated at one or more measurement intervals. Calculated scores may be compared to one or more reference scores. An action may be triggered based on a calculated score and/or based on the relative values of a calculated score and a reference score.

7 Claims, 37 Drawing Sheets

Related U.S. Application Data filed on Jun. 10, 2019, provisional application No. 62/777,333, filed on Dec. 10, 2018.

(51) Int. Cl.
  *G06F 16/22* (2019.01)
  *G06F 16/2455* (2019.01)
  *G16H 80/00* (2018.01)

(56) References Cited

U.S. PATENT DOCUMENTS

| | | |
|---|---|---|
| 2011/0276374 A1 | 11/2011 | Heiser et al. |
| 2012/0054020 A1 | 3/2012 | Jacobs |
| 2014/0052474 A1 | 2/2014 | Mandan et al. |
| 2014/0052475 A1 | 2/2014 | Madan et al. |
| 2015/0324532 A1 | 11/2015 | Jones et al. |
| 2016/0255384 A1 | 9/2016 | Marci et al. |
| 2016/0314784 A1 | 10/2016 | Kleppe et al. |
| 2017/0140398 A1 | 5/2017 | Fleischman et al. |
| 2017/0323065 A1 | 11/2017 | Proctor Beauchamp et al. |
| 2017/0351830 A1 | 12/2017 | Burger et al. |
| 2018/0295418 A1 | 10/2018 | Peterkofsky et al. |
| 2019/0098290 A1* | 3/2019 | Baran ................... H04N 13/122 |
| 2020/0013089 A1* | 1/2020 | Narayan ................. G06F 16/27 |
| 2020/0278969 A1* | 9/2020 | Tran ..................... G06F 16/2433 |
| 2020/0280764 A1* | 9/2020 | Maughan .......... H04N 21/25883 |
| 2020/0302478 A1* | 9/2020 | Martinez ............... H04N 21/812 |
| 2021/0051367 A1* | 2/2021 | Holz ....................... G06Q 30/02 |
| 2021/0090095 A1* | 3/2021 | Sekharan ................ G06N 20/00 |
| 2021/0192576 A1* | 6/2021 | Narayan ................. G06F 16/27 |
| 2021/0279245 A1* | 9/2021 | Ryan .................... G06F 16/2457 |

OTHER PUBLICATIONS

International Search Report and Written Opinion in PCT/US19/65489 dated Feb. 12, 2020.

Salway A., Kelly L., Skadina I., Jones G.J.F. (2010) Portable Extraction of Partially Structured Facts from the Web. In: Loftsson H., Rögnvaldsson E., Helgadóttir S. (eds) Advances in Natural Language Processing. NLP 2010. Lecture Notes in Computer Science, vol. 6233. Springer, Berlin, Heidelberg.

Imel, Zac E., et al., Technology-Enhanced Human Interaction in Psychotherapy, J Couns. Psychol. Jul. 2017.

* cited by examiner

| User_id 1405 | Last name 1410 | First name 1415 | Email 1420 | Nick name 1425 | Date of Birth 1430 | Start Date 1435 | End Date 1440 | Location 1445 | Account Number 1450 | Plan 1455 | Provider Preferences 1460 | Last Payment Received 1465 | Login name 1470 | Password 1475 | Emergency contact 1480 |
|---|---|---|---|---|---|---|---|---|---|---|---|---|---|---|---|
| U2834500 | Jones | Travis | jt@xyz.com | Travis | 9/4/1960 | 2/27/2023 16:56:01 | 6/20/2023 10:41:19 | 85 Central Lane, Green Valley, VT 12345 | 1111-1111-1111-1111 | Monthly | male; age 50+ | 5/31/2023 | Travis 1 | 2dk213% &BN* | Ella Travis, cousin, 111-222-3333 |
| U2834501 | <not given> | <not given> | northstar@lmn.com | River | 1985 | 4/15/2023 8:44:56 | Still active | Utah | 2222-2222-2222-2222 | Quarterly | 5+ years experience | 3/31/2023 | northstar | Sbesa 32% 71@ | <None provided> |
| U2834502 | Peters | Lenny | lpeters@zyx.com | Pete | 8/22/1995 | 5/30/2023 23:09:11 | Still active | 456 Middlebrook Road, Asheville Virginia 98765 | 3333-3333-3333-3333 | Video Only | Spanish speaker | 5/31/2023 | lenny 999 | Poe 3829#129 | Bernard Colsen, Roommate, bernard654 @vft.com |

| Event ID 2105 | User_id 2108 | Event Time 2110 | Event Type 2115 | Elapsed Time (hours) 2120 | Score Immediately Before Event 2125 | Score Increase 2130 | Score Immediately After Event 2135 |
|---|---|---|---|---|---|---|---|
| E38292013 | U3919061 | 1/12/23 10:05 AM | Begin Treatment | N/A | N/A | N/A | 1 |
| E38292014 | U3919061 | 1/12/23 11:00 AM | Hourly Snapshot | 0.92 | 0.94 | 0.65 | 1.58 |
| E38292025 | U3919061 | 1/12/23 11:36 AM | Message | 0.60 | 0.94 | 0.65 | 1.58 |
| E38292036 | U3919061 | 1/12/23 12:00 PM | Hourly Snapshot | 0.40 | 1.55 | 0.00 | 1.55 |
| E38292047 | U3919061 | 1/12/23 1:00 PM | Hourly Snapshot | 1.00 | 1.49 | 0.00 | 1.49 |
| E38292048 | U3919061 | 1/12/23 2:00 PM | Hourly Snapshot | 1.00 | 1.43 | 0.00 | 1.43 |
| E38292049 | U3919061 | 1/12/23 3:00 PM | Hourly Snapshot | 1.00 | 1.37 | 0.00 | 1.37 |
| E38292060 | U3919061 | 1/12/23 3:30 PM | Message | 0.50 | 1.34 | 0.65 | 1.98 |
| E38292061 | U3919061 | 1/12/23 3:45 PM | Message | 0.25 | 1.96 | 0.65 | 2.61 |
| E38292072 | U3919061 | 1/12/23 4:00 PM | Hourly Snapshot | 0.25 | 2.58 | 0.00 | 2.58 |
| E38292073 | U3919061 | 1/12/23 5:00 PM | Hourly Snapshot | 1.00 | 2.47 | 0.00 | 2.47 |
| E38292084 | U3919061 | 1/12/23 6:00 PM | Hourly Snapshot | 1.00 | 2.36 | 0.00 | 2.36 |
| E38292095 | U3919061 | 1/12/23 6:18 PM | Assessment | 0.30 | 2.33 | 1.29 | 3.62 |
| E38292106 | U3919061 | 1/12/23 7:00 PM | Hourly Snapshot | 0.70 | 3.52 | 0.00 | 3.52 |
| E38292117 | U3919061 | 1/12/23 8:00 PM | Hourly Snapshot | 1.00 | 3.37 | 0.00 | 3.37 |
| E38292118 | U3919061 | 1/12/23 9:00 PM | Hourly Snapshot | 1.00 | 3.22 | 0.00 | 3.22 |
| E38292119 | U3919061 | 1/12/23 10:00 PM | Hourly Snapshot | 1.00 | 3.09 | 0.00 | 3.09 |
| E38292120 | U3919061 | 1/12/23 11:00 PM | Hourly Snapshot | 1.00 | 2.96 | 0.00 | 2.96 |
| E38292131 | U3919061 | 1/13/23 12:00 AM | Hourly Snapshot | 1.00 | 2.83 | 0.00 | 2.83 |
| E38292132 | U3919061 | 1/13/23 1:00 AM | Hourly Snapshot | 1.00 | 2.71 | 0.00 | 2.71 |
| E38292143 | U3919061 | 1/13/23 2:00 AM | Hourly Snapshot | 1.00 | 2.60 | 0.00 | 2.60 |
| E38292144 | U3919061 | 1/13/23 2:30 AM | Message | 0.50 | 2.54 | 0.65 | 3.19 |
| E38292155 | U3919061 | 1/13/23 3:00 AM | Hourly Snapshot | 0.50 | 3.12 | 0.00 | 3.12 |
| E38292156 | U3919061 | 1/13/23 4:00 AM | Hourly Snapshot | 1.00 | 2.99 | 0.00 | 2.99 |
| E38292167 | U3919061 | 1/13/23 5:00 AM | Hourly Snapshot | 1.00 | 2.86 | 0.00 | 2.86 |
| E38292168 | U3919061 | 1/13/23 6:00 AM | Hourly Snapshot | 1.00 | 2.74 | 0.00 | 2.74 |
| E38292169 | U3919061 | 1/13/23 7:00 AM | Hourly Snapshot | 1.00 | 2.62 | 0.00 | 2.62 |
| E38292180 | U3919061 | 1/13/23 8:00 AM | Hourly Snapshot | 1.00 | 2.51 | 0.00 | 2.51 |
| E38292181 | U3919061 | 1/13/23 9:00 AM | Hourly Snapshot | 1.00 | 2.41 | 0.00 | 2.41 |
| E38292192 | U3919061 | 1/13/23 10:00 AM | Hourly Snapshot | 1.00 | 2.31 | 0.00 | 2.31 |
| E38292203 | U3919061 | 1/13/23 11:00 AM | Hourly Snapshot | 1.00 | 2.21 | 0.00 | 2.21 |

FIG. 21

| id 2505 | Activity_ cohort_id 2510 | Cohort_day _index 2515 | cohort_sum 2520 | Cohort_sum 2525 | Cohort_count 2530 Cohort_ squared_sum |
|---|---|---|---|---|---|
| Cd392392 | Ac225 | 1 | 4.42 | 6 | 6.86 |
| Cd392401 | Ac225 | 2 | 4.15 | 6 | 4.69 |
| Cd392411 | Ac225 | 3 | 10.73 | 6 | 24.63 |
| Cd478174 | Ac225 | 56 | 10.92 | 6 | 25.52 |
| Cd510031 | Ac233 | 1 | 4.58 | 4 | 5.58 |

SYSTEM AND METHOD FOR MONITORING ENGAGEMENT

The present application claims the benefit of U.S. provisional patent application No. 62/876,954, entitled "System and Method for Auto-Generating Summaries of Messaging-Based Interactions Between Patients and Healthcare Providers", and filed Jul. 22, 2019; U.S. provisional patent application No. 62/777,333, entitled "System and Method for Monitoring Client Engagement in Behavioral Healthcare", and filed Dec. 10, 2018; and U.S. provisional patent application No. 62/859,659, entitled "System and Method for Monitoring Provider Engagement in Behavioral Healthcare", and filed Jun. 10, 2019, the entirety of each of which are hereby incorporated by reference herein for all purposes.

BACKGROUND

Remote services can be beneficial. Health services can be beneficial. Remote health services can be beneficial. Mental health services can be beneficial. Remove mental health services can be beneficial.

Face-to-face appointments with service providers, such as medical service providers and/or mental health service providers, can be expensive. Service providers may have limited availability, meaning face-to-face meetings may not occur at preferred times for service recipients (e.g., patients).

Service providers may not be located near to service recipients, meaning recipients may require time-consuming travel if they are to meet with providers. Even if there are service providers near to a service recipient, the number of such service provides may be limited and none of them may be especially well-suited to a prospective service recipient.

It may be difficult for providers of remote services to track the activity, engagement or interest level of clients. As such, it may be difficult for the providers restore the flagging interest of clients and avert stunted progress or departure of such clients.

SUMMARY

In various embodiments, an activity level of service recipients is determined and stored. Service providers may view such activity levels. Service providers may thereby have the opportunity to adjust their methods for delivering services based on the recipient activity levels.

BRIEF DESCRIPTION OF THE FIGURES

FIG. 14 shows a data structure storing user information according to some embodiments.
FIG. 21 shows a data structure storing engagement metrics according to some embodiments.
FIG. 25 shows a data structure storing summary engagement metrics for cohorts according to some embodiments.

DESCRIPTION

As used herein, and unless otherwise specified, the terms "client", "customer", "user", "patient", "service recipient", "consumer" refer to consumers of services, mental health services, behavioral health services, medical services, professional services, and/or other services described herein.

As used herein, and unless otherwise specified, the terms "provider", "therapist", "psychotherapist", "medical professional", refer to providers of services, mental health services, medical services, professional services, and/or other services described herein.

As used herein, and unless otherwise specified, the term "platform" refers to an integrated set of technologies and business processes that make it possible for consumers and providers to connect and communicate with one another, and that make it possible for consumers to receive potentially beneficial information and services. In various embodiments, a platform may include a system comprising a server connected to a network, where the server is programmed to communicate with both consumer and provider devices over the network, and where the server is programmed to facilitate communication between consumer and provider devices.

Figure 1:
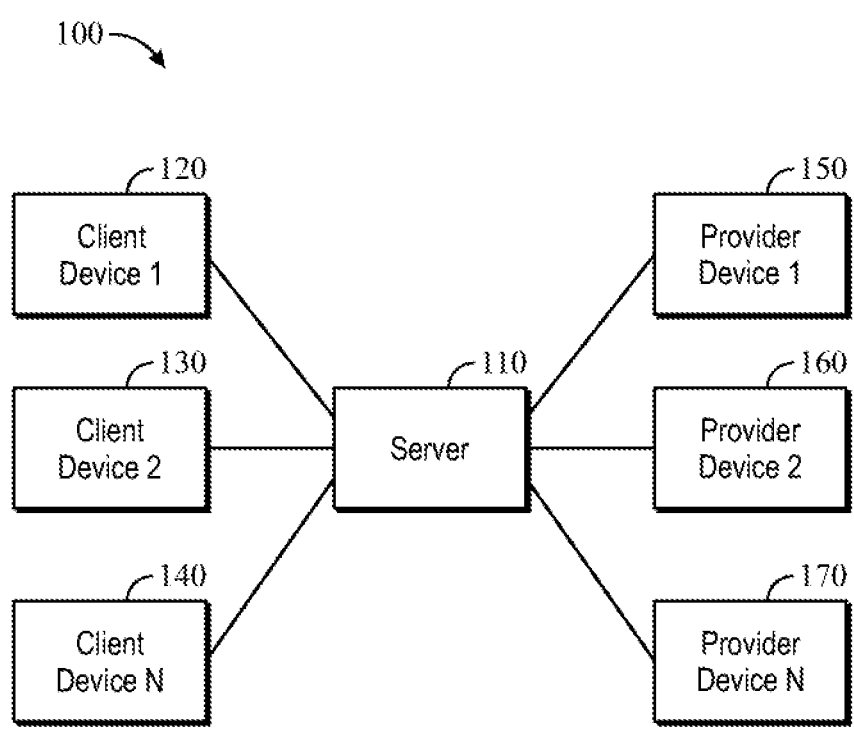
FIG. 1 shows a system according to some embodiments.

FIG. 1 shows a system 100 for an exemplary platform (e.g., a web-based computing platform) according to some embodiments.

Server 110 is in communication with one or more client devices (e.g., client devices 120, 130, 140) and with one or more provider devices (e.g., provider devices 150, 160, 170).

Client and provider devices may include a smart phone, cellular phone, a personal digital assistant, a laptop, a watch, a smart watch, a personal computer, a laptop, a netbook, a portable computer, an Apple computer, a desktop computer, a workstation, a server, a pager, a game console, a set-top box, a smart picture frame, an electronic reader, an Apple iPad, a slate computer, a tablet computer, and/or any other computing device, and/or any other electronic device and/or any other device.

Server 110 may include one or more of a physical server, a virtual server, a distributed server, and a cloud server.

Server 110 may communicate with client and provider devices via one or more networks (e.g., via the Internet).

In operation, the server 110 may serve web pages, application pages (e.g., pages or screens of apps for Android, iOS, etc.) or any other pages, or any other content, to client or provider devices. Clients and providers may interact with such web pages, application pages, or other content, such as by entering text, uploading or attaching media (e.g., images, video, audio, etc.), touching or clicking on buttons or links or other active content, scrolling, navigating, expanding, reducing, or interacting in any other fashion. Client and provider devices may also interact with server 110 by gathering device data (e.g., motion data, accelerometer data, gyroscope data, orientation data, data about when the device is on, data about when the device is connected to a network, data about when the device is in use, keystroke data, touch data, camera data, eye tracking data, etc.), possibly storing such data, and transmitting such data to the server.

In various embodiments, system 100 may enable text, audio, and/or video-based communication between providers (e.g., psychotherapists) and clients (e.g., the providers' patients). In various embodiments, the system includes a web-based user-interface through which a client interacts with the platform to send and receive messages from their provider (e.g., their behavioral health care provider), and carry out other activities. Other activities may include completing a survey or a mindfulness exercise. In various embodiments, system 100 may include one or more servers (e.g., compute servers) that process events performed on the platform and perform calculations, and one or more databases. The one or more databases may store attributes associated with one or more clients (e.g., with all clients) and one or more providers (e.g., with all providers) using the platform. The databases may store information associated with one or more events (e.g., with each event) that occurs on the platform, such as the length of a message, the sender of a message, and its timestamp, etc.

Figure 2:
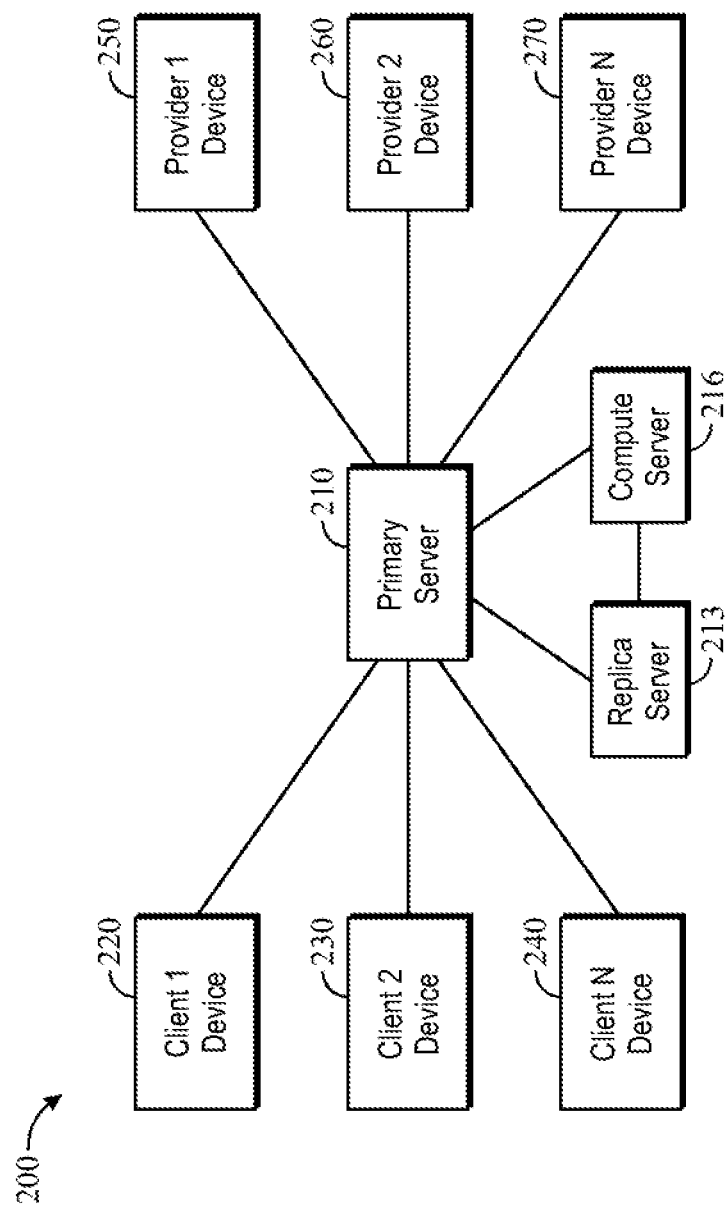
FIG. 2 shows a system according to some embodiments.

FIG. 2 shows a system 200 for an exemplary platform according to some embodiments. System 200 may include a primary server 210 that, among other things, may store atomic data, primary data, and/or granular data, such as data gathered directly from client or provider devices. Replica server 213, in communication with the primary server, may periodically copy data (e.g., new data, e.g., all existing data) from the primary server with the objective of maintaining a copy of the data in the primary server. In various embodiments, certain business logic may be executed using data from the replica server 213. Such business logic may include computing secondary data, such as summary or aggregate measures based on the more granular data copied from the primary server. Examples of summary or aggregate measures may include the total number of messages sent by a provider within a given hour. Where 'read' operations are performed on the replica server, there is a reduced chance of erroneously deleting or otherwise corrupting the data stored on the primary server.

In various embodiments, system 200 may include a compute server 216. In various embodiments, the compute server 216 may carry out business logic, computations, etc., that are not critical or not immediately critical or not required in real time. The compute server may store secondary, computed, calculated, derived, etc., data based on the outputs of business logic. For example, business logic may input primary data from the replica server 213, and output secondary data that is written to compute server 216. Where 'write' operations are performed on the compute server 216, there may be a reduced chance of corrupting data on the primary server 210 or replica server 213.

In various embodiments, where business logic involves both read and write operations, and where read operations are performed on a first server (e.g., replica server 213), and write operations are performed on a second server (e.g., on compute server 216), the performance of the business logic (e.g., speed of execution) may be enhanced.

Figure 3:
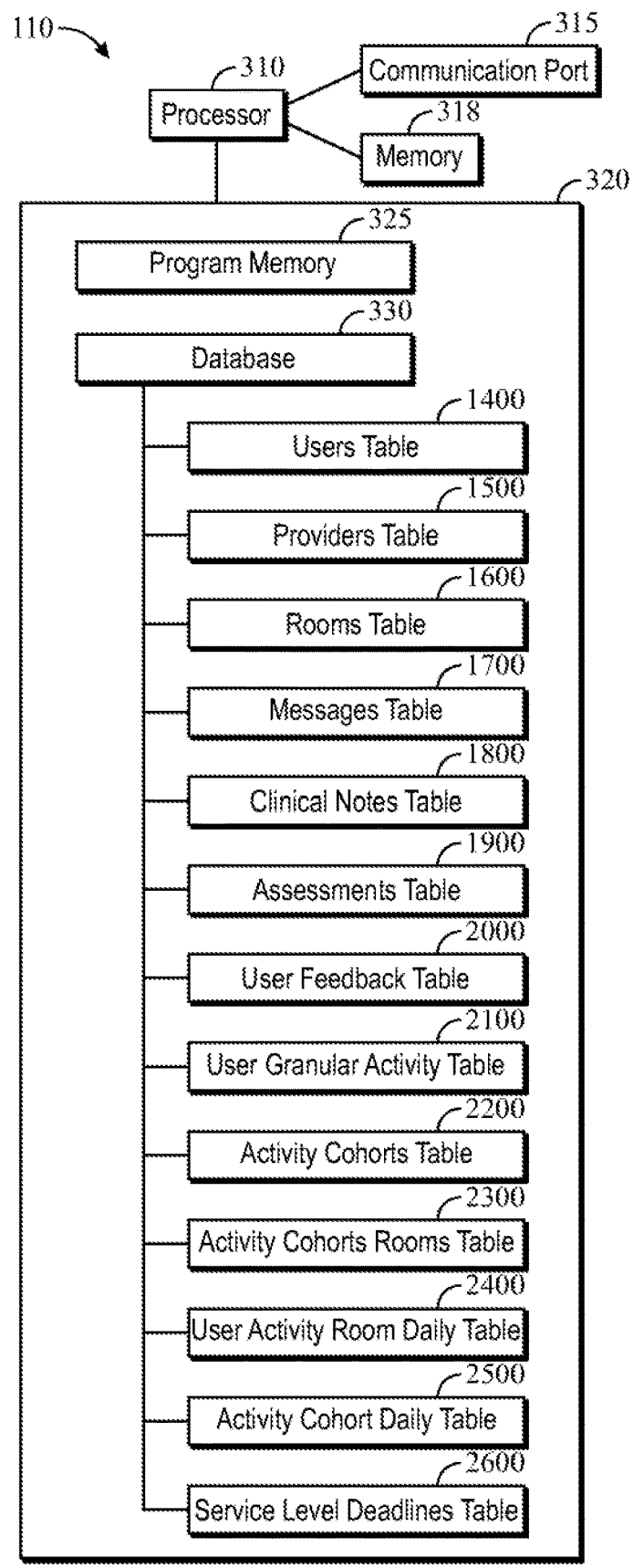
FIG. 3 shows a block diagram of a server according to some embodiments.

With reference to FIG. 3, a server 110 is shown according to some embodiments. A processor 310 is in communication with a communications port 315, memory 318, and storage 320. The processor may be any integrated circuit, set of logic gates, discrete signal processor, controller, central processing unit, graphics processing unit, tensor processing unit, or any other device capable of executing instructions, such as computer instructions.

Memory 318 may be any suitable type of memory, including random access memory (RAM), read-only memory (ROM), etc.

Storage 320 may include any suitable type of memory, such as secondary memory, and may include hard drives, magnetic memory, optical memory, holographic memory, or any other type of memory. Storage 320 may include program memory 325, which may store computer code, computer instructions, or other logic for execution by the processor 310 or by any other component. In various embodiments, for example, code in program memory 325 may be copied to memory 318 when in use, and otherwise may be stored long-term in program memory 325.

Storage 320 may include a database 330. Database 330 may include one or more tables for storing data structures, such as rows of related data. In various embodiments, database 330 may store one or more of: a users table 1400, for storing information about users; a providers table 1500 for storing information about providers; a rooms table 1600 for storing information about relationships between clients and providers; a messages table 1700 for storing information about messages, such as messages communicated between a client and provider; a clinical notes table 1800 for storing information about clinical notes, such as notes that might be recorded by a provider of therapeutic or other medical services; an assessments table 1900 for storing information about assessments given to users, such as clinical assessments; a user feedback table 2000 for storing feedback that users have provided, such as feedback about the platform; a user granular activity table 2100 for storing information about user activity on the platform; an activity cohorts table 2200 for storing categories for cohorts of users; activity cohorts rooms table 2300 for storing assignments to cohorts (e.g., assignments of users and/or user rooms to cohorts); a user activity room daily table 2400 for storing engagement metrics (e.g., values of engagement metrics calculated on an hourly basis); activity cohort daily table 2500 for storing summary engagement metrics for cohorts (e.g., a total activity score summed over an entire cohort); and a service level deadlines table 2600 for storing deadlines by which providers must meet service obligations (e.g., deadlines to reply to an earlier client message).

It will be appreciated that, in various embodiments, aforementioned tables may serve additional purposes not explicitly mentioned. In various embodiments, storage 320 may store additional tables, or only a subset of the aforementioned tables. In various embodiments, data from the aforementioned tables may be combined into a single table, split up into multiple tables, or stored in any practicable fashion. In various embodiments, data need not be stored in tables nor even in a database. In various embodiments, data may be stored or maintained in any suitable structure and in any suitable environment.

In various embodiments, memory 318 may store computer instructions, computer code, and the like, for execution by the processor in accordance with various embodiments. Computer code may include structured query language (SQL) scripts, Python scripts, HTML, JavaScript, React, Django, Java, C, Objective C, Bash, and/or any other type of computer code.

Communications port 315 may comprise a network interface, network interface card, an antenna, a receiver, a transceiver, and/or any other suitable component. The communications port 315 may receive and/or decode messages, signals, information, etc., from other devices, such as other devices on a network (e.g., on the Internet, e.g., on a cellular network). The communications port 315 may transmit and/ or encode messages, signals, information, etc., to other devices, such as other devices on a network. Aforementioned 'other devices' may include user devices and provider devices.

Received signals may be stored in memory 318 and/or relayed to the processor 310. Likewise signals generated by the processor 310 may be relayed to the communications port 315 for transmission to other devices, or temporarily stored in memory 318 and subsequently relayed to the communications port 315 for transmission to other devices.

It will be appreciated that hardware, components, devices and the like described herein need not be individual, physically bounded, or even physical at all, in various embodiments. For example, in various embodiments, processor 310 may comprise multiple physical processors coordinating their operations. In various embodiments, processor 310 may comprise one or more cores from a larger processor. In various embodiments, processor 310 may be a virtual processor. A virtual processor may, for example, use a subset of the computing cycles from one or more physical processors. Similarly, memory 318 may comprise multiple physical memories across different components, where such components may be physically and even geographically dispersed.

Figure 4:
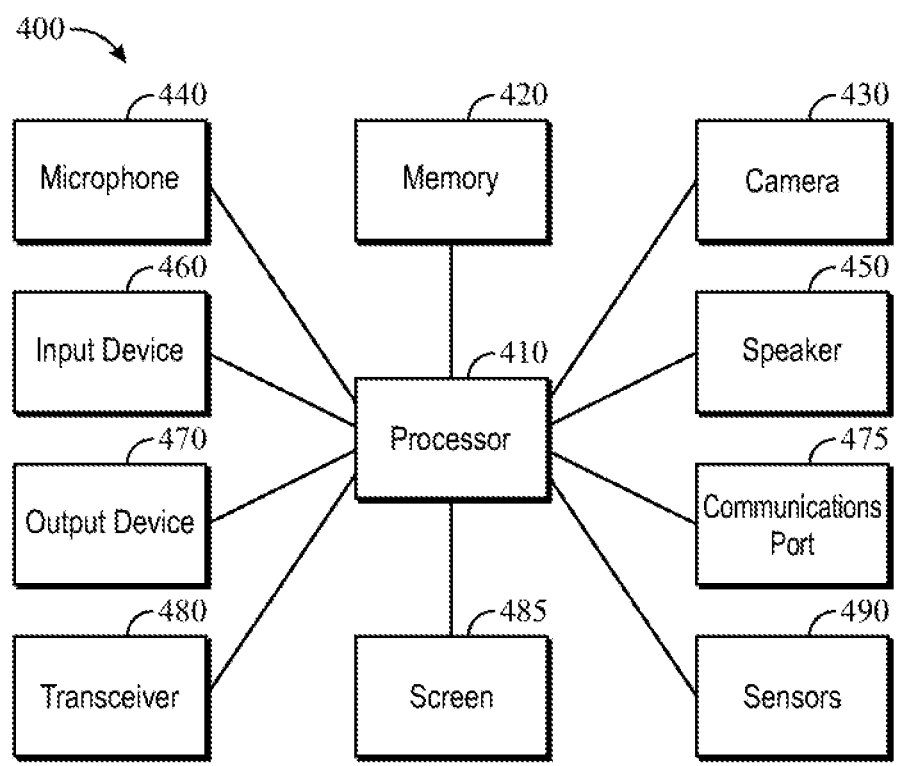
FIG. 4 shows a block diagram of a client device according to some embodiments.

With reference to FIG. 4, a client device 400 is shown according to some embodiments. The client device may include a processor 410. The processor may be in communication with memory 420, camera 430, microphone 440, speaker 450, input device 460, output device 470, communications port 475, transceiver 480, screen 485, and sensors 490.

Memory 420 may include random access memory (RAM), read-only memory (ROM), hard drives, or any other type of memory. Memory 420 may store data, files, images, bytes, binary files, content, information, videos, or any other data used in accordance with various embodiments. Memory 420 may store software instructions, computer instructions, software code, computer code, logic, and/or any other instructions for operating processor 410 in accordance with various embodiments. Memory 420 may include storage for temporary data, intermediate data, variables, etc., used during execution of logic (e.g., business logic) in accordance with various embodiments.

Camera 430 may include hardware and/or software for capturing images and/or video. Microphone 440 may include hardware and/or software for capturing sound (e.g., for capturing spoken audio messages). Speaker 450 may include hardware for outputting sound. Input device 460 may include buttons, dials, keys (e.g., alphanumeric keys), switches, styluses, touchpads, touch screens, computer mice, trackballs, keyboards, keypads, joysticks, and/or any other means for receiving human input.

Output device 470 may include screens, microphones, lights, speakers, vibrating components, haptic devices, or any other device or component for generating outputs.

Communications Port 475 may include a network interface card or any other interface to a network, or any other means of receiving and/or transmitting signals, messages, information, etc.

Transceiver 480 may include a transmitter, receiver, combination transmitter/receiver, antenna, etc. The transceiver may be capable of transmitting and/or receiving electromagnetic signals, such as cellular signals, wireless signals, Wi-Fi signals, Bluetooth signals, etc.

Using one or more of communications port 475 and transceiver 480, client device 400 may be capable of communicating with external devices (e.g., with server 300). The client device 400 may be capable of communicating with and/or via a network (e.g., the Internet, e.g., the cellular network).

Screen 485 may include a cathode ray tube (CRT) screen, light-emitting diode (LED) screen, organic light-emitting diode (OLED) screen, plasma screen, liquid crystal display (LCD) screen, electronic ink (e-ink) screen, display screen, computer screen, computer monitor, etc., for outputting text, images, video, visual output, etc. Screen 485 may also function as a touchscreen, in various embodiments. The touchscreen may sense operator touches. The touchscreen may sense a location of operator touches. The touchscreen may sense multiple simultaneous operator touches. The touchscreen may sense operator motions, such as swipes.

Sensors 490 may include touch sensors, touch screens, accelerometers, positional sensors, geographic sensors, global positioning system (GPS) sensors, microphones, vibration sensors, impact sensors, light sensors, or any other sensors.

Figure 5:
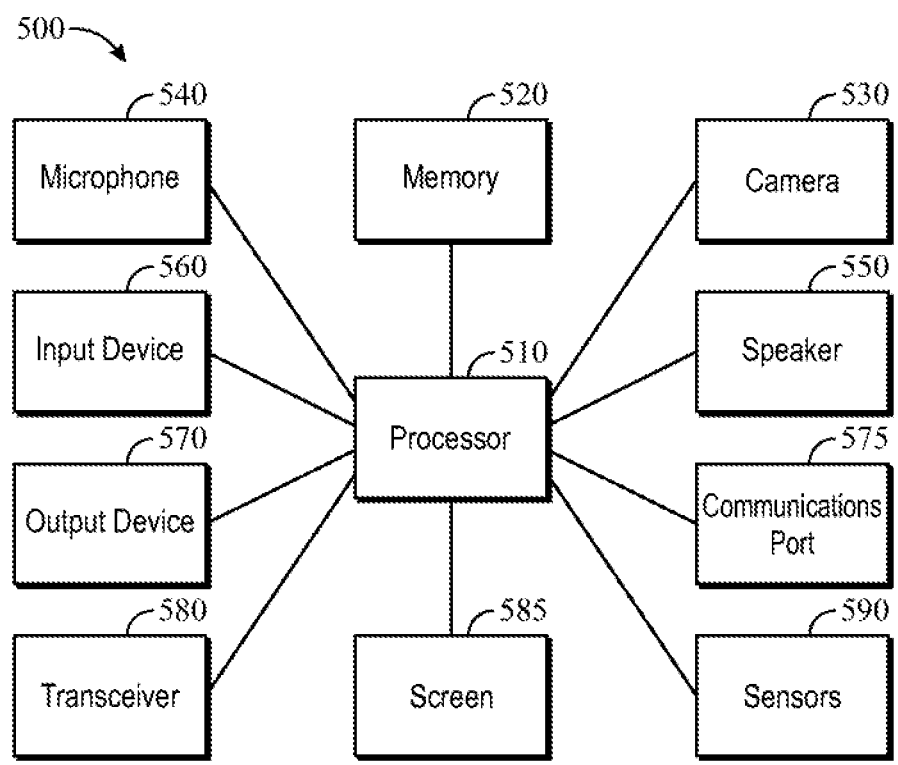
FIG. 5 shows a block diagram of a provider device according to some embodiments.

With reference to FIG. 5, a provider device 500 is shown according to some embodiments. A provider device may be similar to, or the same as a client device in terms of construction and operation. Thus, a provider device will not be described in detail as a client device has already been described.

Figure 6:
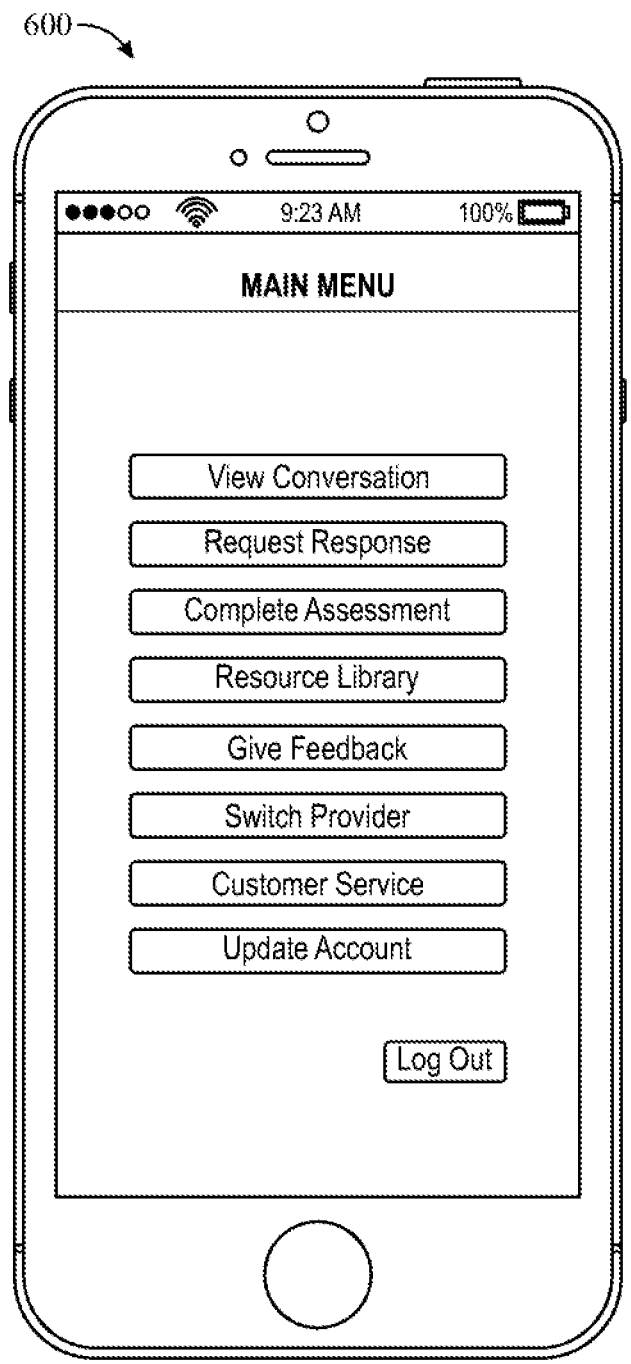
FIG. 6 shows a graphical interface according to some embodiments.

With reference to FIG. 6, a user interface for a client is depicted according to some embodiments. The user interface may represent a screen of an app, such as an app on a smart phone (e.g., on an Android phone or Apple iPhone). In various embodiments, this or a similar user interface may appear on any other suitable device. The user interface may appear on a client device, such as on Client 1 Device 120.

The user interface of FIG. 6 may represent a main menu, dashboard, main dashboard, home screen, or the like, from which a user may select one or more tasks. Upon selecting a task, one or more programmatic actions may be triggered on the user device, such as loading a new screen, initiating a phone call, or using any other functionality of the device. A "view conversation" button may, when activated (e.g., touched) take the user to a screen where there are listed historical messages between the user and the provider. A "request response" button may allow the user to specify a deadline by which the user wishes the provider to respond to the user (e.g., to the user's most recent message to the provider). A "complete assessment" button may take the user to a screen where the user can complete an assessment (such as a clinical assessment). A "resource library" button may allow the user to access one or more resources, such as resources other than the user's provider. Resources may include informational articles (e.g., articles about the user's health condition), videos, talks, journal articles, scientific articles, statistics (e.g., about the prevalence or prognosis for the user's health condition), support resources, emergency hotlines, blogs, social media pages (e.g., related to the user's health condition), or any other resources.

A "give feedback" button may allow the user to provide feedback, such as feedback about the platform. A "switch provider" button may allow the user to switch, or request to switch, to a new provider. A "customer service" button may allow the user to contact customer service (e.g., by phone, live chat, etc.), or may point the user towards a way of doing so (e.g., providing an email address or phone number). An "update account" button may allow a user to change one or more items about the user's account or profile, such as a nickname, address, financial account information, provider preferences, availability, service plan (e.g., "monthly" plan versus "quarterly" plan), account status (e.g., the user may put his account on hold, the user may indicate he wishes to stop receiving services altogether, the user may indicate he wishes to resume services after a hold), or any other aspect of the user's account.

It will be appreciated that, although the present description may refer to a "button" or "buttons" on a user interface, various embodiments envision that any other type of input mechanism may be used, including use of dials, scroll bars, swipes, voice input, etc. Various embodiments described herein have shown buttons with particular labels. However, it will be appreciated that alternative labels may be used, in various embodiments. Such alternative labels may include other text, or non-text indicators such as coloring, texture, position on the screen, and so on.

The foregoing has described some functionality available to users according to some embodiments. However, various embodiments contemplate that additional functionality may be available to users. Various embodiments contemplate that some of the foregoing may not be available to users. Various embodiments contemplate that certain functionality may be available to users through different means, pathways, etc. For example, in various embodiments, a user may have to navigate through multiple layers of screens in order to accomplish some functionality. In various embodiments, functionality may be available through different or alternative buttons, or through buttons labeled in a different fashion.

As described herein, a user may view or interact with screens to accomplish various functionality or objectives. It will be appreciated that, in various embodiments, the steps to accomplish a given objective may take the user to more than one screen. For example, a user may complete an assessment with four questions by interacting with four separate screens, each screen containing a single question. In various embodiments, there need not be a fine distinction between a first screen and a second screen. For example, as a user interacts with an application, content visible on half of the screen may change, while content on the other half remains stable. As another example, text or images may change while a background remains the same. As another example, a user may zoom into a portion of what is shown on a screen to review details that were otherwise invisible or inaccessible. As another example, a user may scroll down or otherwise shift to a portion of a screen that had previously been out of view.

Various embodiments contemplate that a user may interact with a user device in any suitable fashion, whether the interaction involves static screens, static content, dynamic screens, dynamic content, movies, animations, scrolling elements, panning, zooming, or any other type of interaction. Further, the user may interact with any number of screens or with any quantity of content.

Figure 7:
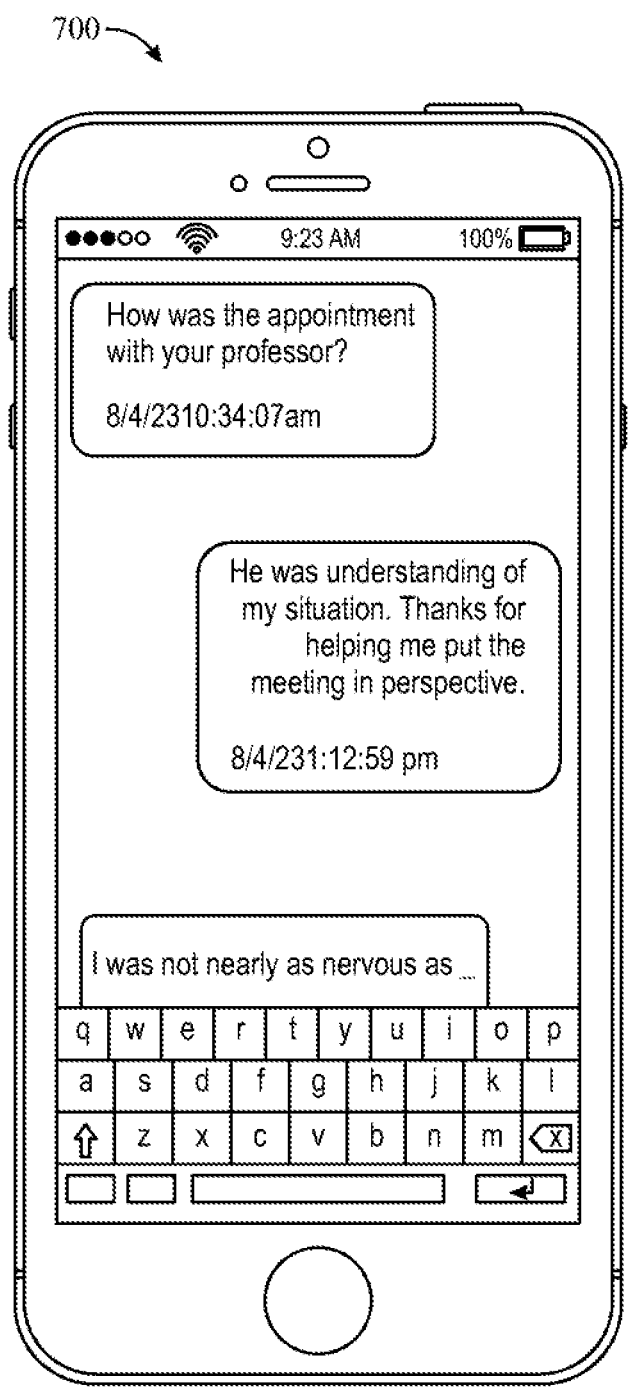
FIG. 7 shows a graphical interface according to some embodiments.

With reference to FIG. 7, a user interface for a client is depicted according to some embodiments. There is shown a history of text messages that have been communicated between the client and the client's provider. In various embodiments, messages from the provider to the client are shown left-justified, while messages from the client to the provider are shown right-justified. In various embodiments, client and provider messages may be distinguished in other ways, such as through coloring, patterning, etc.

As there may be limited screen space, and possibly many historical messages, all messages may not always be visible at once. In various embodiments, it may be possible for the client to see additional historical messages by scrolling, selecting other pages (e.g., the historical conversation may be paginated), and so on. In various embodiments, by default (e.g., when the client initially accesses the conversation from another screen), the most recent messages may be visible.

FIG. 7 depicts a text-entry element where a new message is in the process of being composed. For composing a message, a keyboard (e.g., virtual keyboard) may be utilized. In various embodiments, it may be possible to attach a file (e.g., an image, video, or audio clip) to a message, such as by actuating the "paper clip" icon and locating, on the client's device, the desired file to attach. When the client is ready to send a message, the "send" icon (e.g., the icon resembling a paper airplane) may be activated.

In various embodiments, messages may include time stamps, which may represent the dates and/or times when the message was received.

In various embodiments, the view or interface depicted in FIG. 7 may be referred to as a "room". That is, the client has come to the "room" where he is interacting with the provider and receiving services, such as medical or psychotherapy services.

Figure 8:
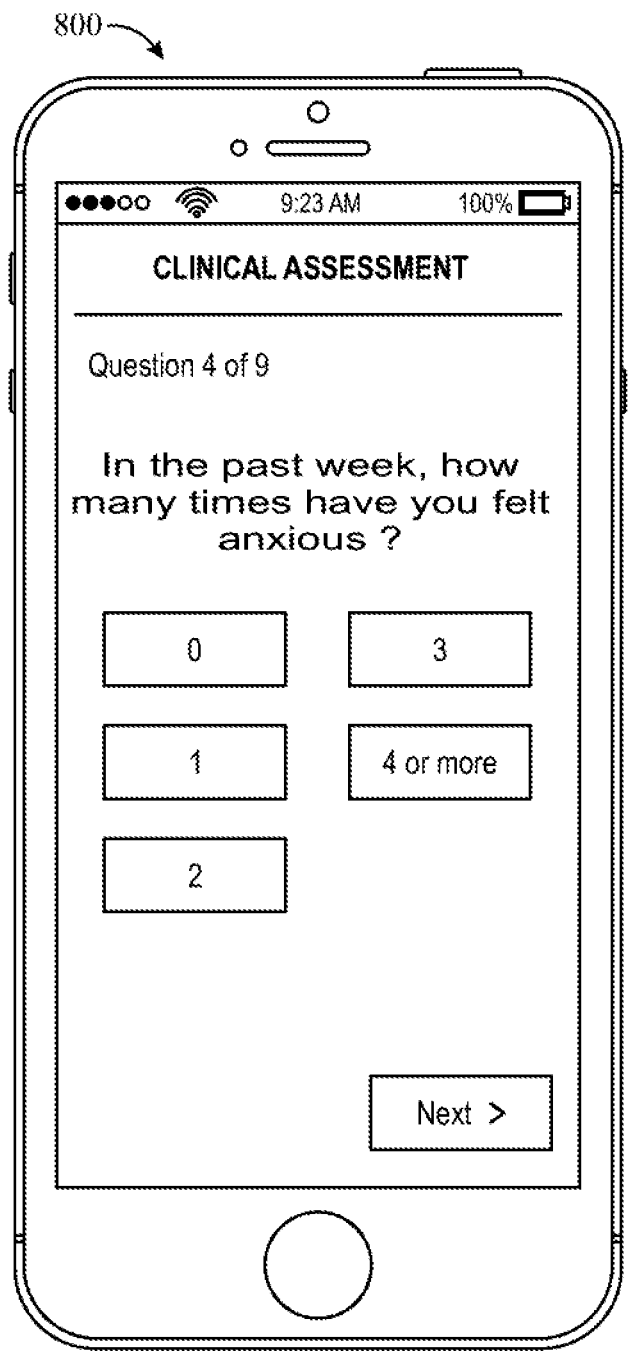
FIG. 8 shows a graphical interface according to some embodiments.

With reference to FIG. 8, a user interface for a client is depicted according to some embodiments. The depicted screen is for a question on an assessment. In this case, the client must navigate through nine different screens to answer all nine questions. The client answers the given prompt by selecting (e.g., pressing) one of the answer choices. When done, the client can press "Next" to go to the next question. As will be appreciated, an assessment may be given in various other ways. For example, the client may also have the opportunity to go "Back" to change earlier answers. As another example, the entire assessment may be on a single screen or page (possible involving scrolling). In various embodiments, an assessment may take a branching form, where the next questions depends on the user's last answer.

Figure 9:
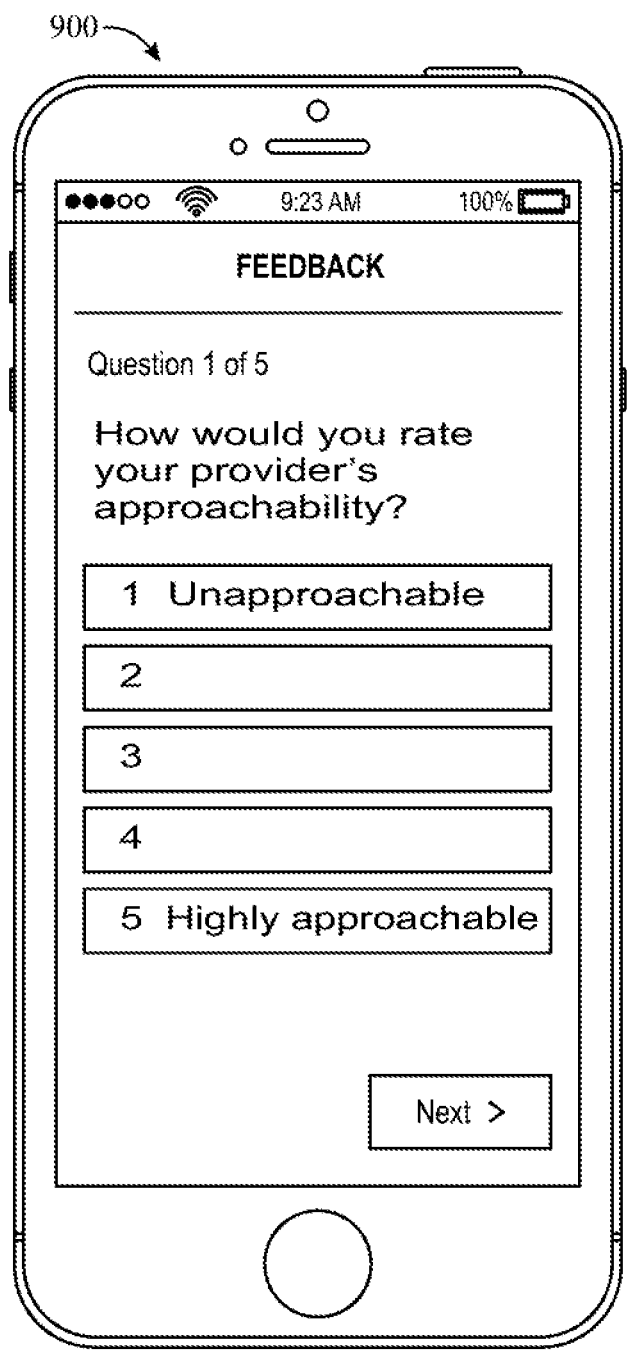
FIG. 9 shows a graphical interface according to some embodiments.

With reference to FIG. 9, a user interface for a client is depicted according to some embodiments. The depicted screen is for a question on a feedback survey. In this case, the client must navigate through five different screens to answer all five questions. The client answers the given prompt by selecting (e.g., pressing) one of the answer choices. When done, the client can press "Next" to go to the next question. As will be appreciated, the client may provide feedback in various other ways.

Figure 10:
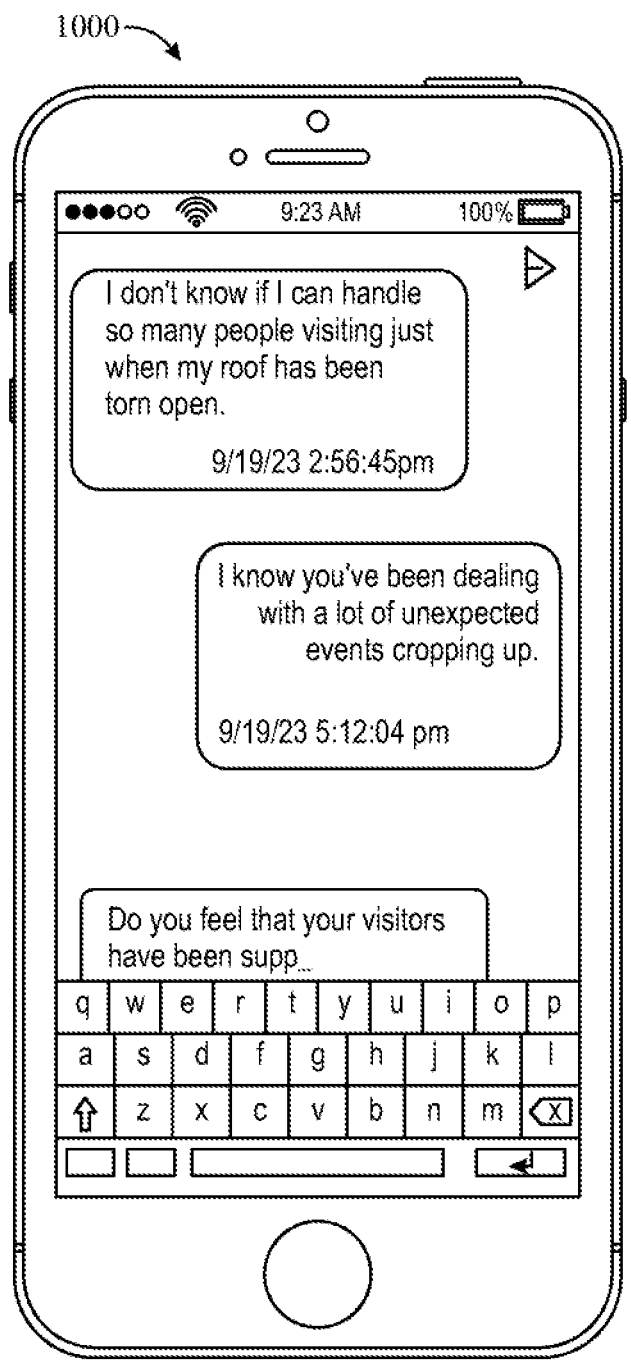
FIG. 10 shows a graphical interface according to some embodiments.

With reference to FIG. 10, a user interface for a provider is depicted according to some embodiments. There is shown a history of text messages that have been communicated between the provider and provider's client. This interface may be similar in many respects to the client's interface (see FIG. 7), so will not be described in as much detail.

Though not shown, in various embodiments the provider's interface may include an indication of a deadline by which the provider must send the next message to the client. This deadline may take the form of a time printed in bold font. In various embodiments, the client's most recent message may be shown in a different color (e.g., different color font, e.g., different background color) depending on when a response is due. For example, if a response is due in the next five minutes, the client's most recent message may be shown in bright red, whereas the client's most recent message might otherwise be shown in green.

Figure 11:
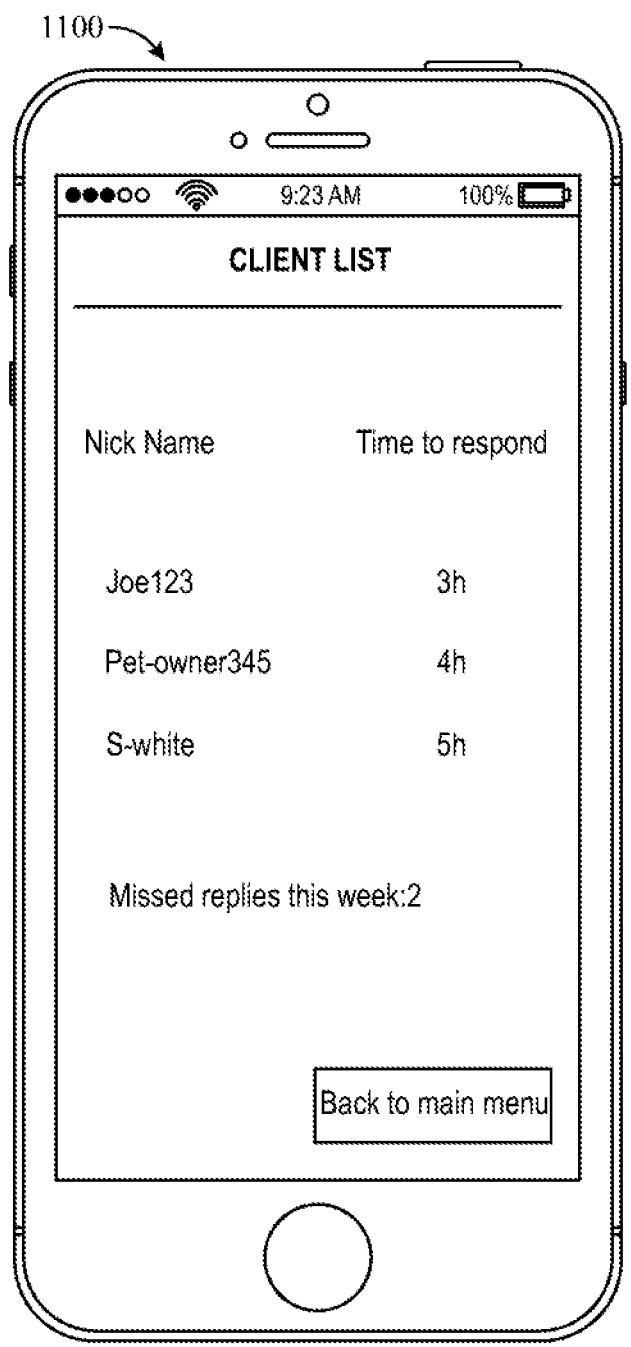
FIG. 11 shows a graphical interface according to some embodiments.

With reference to FIG. 11, a user interface for a provider is depicted according to some embodiments. As depicted, a provider can view a list of his active clients (e.g., using their nicknames). If necessary, a provider may scroll or otherwise navigate to see additional clients. There is also indicated a "time to respond", i.e., the amount of time the provider has remaining to send a message to each respective client in order to meet the provider's obligation to such client. For example, the provider has three hours remaining to respond to "joe123". As will be appreciated, other types of obligations may be displayed.

FIG. 11 additionally indicates a summary metric indicating the provider's historical adherence to his obligations. In this case, the provider has missed two replies in the past week (e.g., the provider has failed twice in the past week to respond to some client's message by the deadline for service).

In various embodiments, if a provider fails to meet a service obligation, such as replying to a customer's message by a particular deadline, then the customer may request (e.g., via the customer's user interface) some type of compensation. Compensation may include, in various embodiments, a refund, free services for some period of time, a discount on services, enhanced services, a gift card, money, or any other form of compensation.

Though not shown, in various embodiments, a provider may use one or more graphical interface elements to set his availability days. The system may take into account the provider's availability when calculating deadlines that the provider must meet, e.g., if the provider indicates he/she is not available on a weekend, then no deadline will be set for a weekend.

Returning to FIG. 11, in various embodiments, a provider may select a client's nickname and thereby navigate to the room where he/she interacts with the selected client (see FIG. 10).

A "back to main menu" button may allow the provider to return to a main menu or dashboard from which the provider may select other functionalities.

Process Flows

Figure 12:
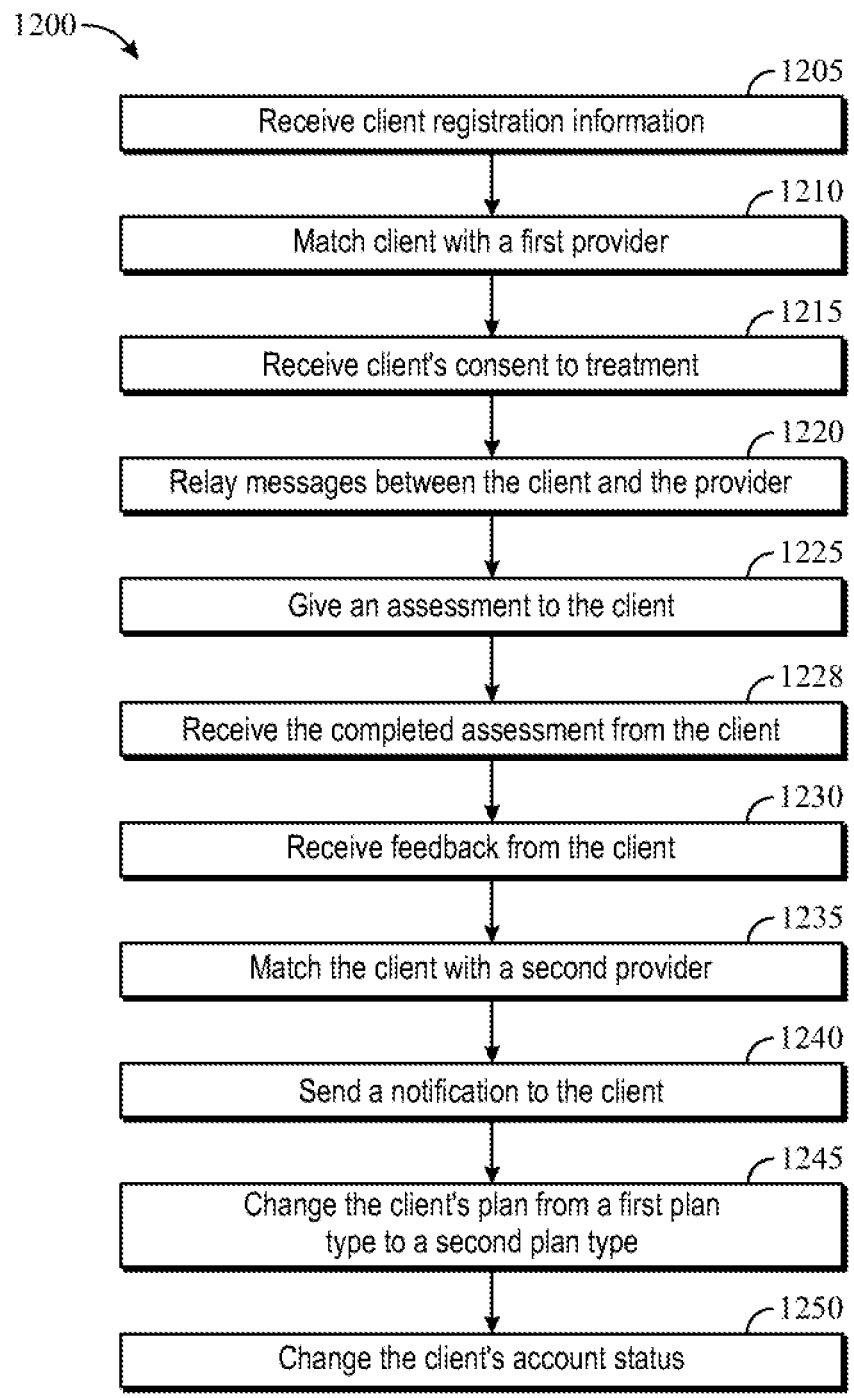
FIG. 12 shows a flow diagram of a user's interaction with a system according to some embodiments.

With reference to FIG. 12, an exemplary user process flow 1200 is shown according to some embodiments.

At step 1205, a user registers with the platform. Registering may include one or more of: selecting a username; selecting a password; providing a date of birth; providing an age; providing an age range; providing proof of age (e.g., providing a driver's license, passport, etc.); providing parental consent (e.g., if a user is under a certain age, the user may be required to obtain and submit parental consent prior to utilizing the platform); providing an address; providing a location (e.g., a state, a city, a country, and/or any other location); providing other demographic information (e.g., race, ethnicity marital status; and/or any other demographic information); providing one or more items of medical history (e.g., indicating any previous experience with psychotherapy); providing a consent to treatment, providing an email address; providing a phone number; providing a mailing address; providing any other contact information; providing emergency contact information (e.g., providing the phone number of a close relative to be contacted in case an emergency arises with the user); providing reasons or motivation for seeking services (e.g., psychotherapy treatment); indicating any current medical and/or psychological issues (e.g., indicating experiences of stress or depression); indicating any prior medical and/or psychological issues; indicating any preferred or desired characteristics of a provider (e.g., indicating the preferred gender, age range, language, treatment style, and/or area of expertise of a provider and/or any other characteristic of a provider); indicating a device the user will be using for interacting with the platform (e.g., indicating a unique identifier for a user's mobile device; e.g., indicating the operating system of the user's device; e.g., indicating the manufacturer of the user's device); and/or providing any other information.

Registration may further include obtaining, reading, viewing, listening to, or otherwise perusing information on what to expect from services to be provided. For example, the user may be informed of how long a typical user might expect to require before seeing improvement in symptoms. The user may be informed of when or how often to expect to hear from the provider. The user may be advised of how much engagement and interaction the user should put forth in order to increase the likelihood of benefit (e.g., of symptom improvement). After perusing information, the user may indicate (e.g., by checking a box) that the user has perused and/or understood such information.

Registration may further include selecting a level of services for the user to receive. The level of services may correspond to a particular "plan". An exemplary plan may include unlimited text messaging with the provider. Another exemplary plan may include unlimited text messaging plus 1 monthly synchronous video call with the provider. As will be appreciated, a variety of plans are possible and contemplated according to various embodiments.

In various embodiments, a plan may include a duration of services and/or a schedule for renewing services. For example, a first plan may require monthly payment by a user, while a second plan may require payment only once every three months by the user. The latter plan may correspond to a lower monthly rate than does the former, but may require more money up front. As will be appreciated, many other durations and/or schedules for renewing services are possible and are contemplated according to various embodiments.

Registration might further include providing payment information. Payment information may include credit or debit card information, bank account information, PayPal account information, Venmo account information, and/or any other financial account and/or any other account information. In various embodiments, a user may provide coupon, promotional, and/or voucher information that may allow a user to receive discounted or even free services for some period of time.

In various embodiments, a user may provide insurance information. The user's insurance carrier may thereupon cover some or all the costs of services provided to the user.

In various embodiments, a user may provide employer information. Such information may include the name of an employer, an employer identification number (EIN), a unique code provided to the employer by the platform, or any other employer information. The user may also provide proof of employment, such as an employee badge, an email address at the employer's domain, a paycheck, an employer-provided tax form, a unique code given to the employee from the employer, and/or any other proof of employment. The employer may thereupon cover some or all the costs of services provided to the user. For example, the employer may cover costs of treatment as part of an Employee Assistance Program (EAP).

In various embodiments, registration may include a free consultation. The consultation may be between the user and a provider. The provider need not necessarily be the same provider that ultimately provides services (e.g., treatment) to the user.

At step 1210, the user is matched to a provider. The matching process may consider any preferences the user has expressed as to the characteristics of a provider. The matching process may also consider availability of providers, location of providers (e.g., a user may be matched with a provider in his/her home state), experience level of providers, and/or any other feature or characteristic of a provider. In various embodiments, a user may only be matched with a provider licensed to practice in the user's state of residence. Ensuring that a provider is licensed in the user's state may comply with state laws.

In various embodiments, the matching process may occur in multiple steps. First, the platform may select a limited number of providers as candidate matches for the user (e.g., the platform may select 3 candidate matches). The user may then have the opportunity to learn more about each of the candidate matches (e.g., by reading the matches' profiles/biographies, by looking at the matches' photos, etc.). Next the user may select one of the candidate matches. In various embodiments, the user may decide that none of the candidate matches are of interest, and may request a new set of candidate matches, in which case the process may repeat.

At step 1215, the user may indicate his/her consent to treatment by the particular provider with which the user has been matched. For example, the user may affix an electronic signature to a consent form that he/she has been provided and has read through.

At step 1220, the user and the provider may exchange one or more messages. In various embodiments, the messages may be text messages, asynchronous audio messages (e.g., audio recordings), asynchronous video messages (e.g., video recordings), images, GIFs, animations, synchronous video messages (e.g., live video calls involving both provider and user at the same time), synchronous audio messages (e.g., live audio calls involving both provider and user at the same time; e.g., phone calls), and/or any other messages. Messages may be visible to the user and provider as a time-ordered sequence of messages leading from the past to the present. In various embodiments, all messages are transmitted in encrypted format and stored in encrypted format.

At step 1225, an assessment may be given to the user. The assessment may be a clinical assessment. The assessment may ascertain the user's current level of symptoms (e.g., how severely stressed is the user at the moment). The assessment may contain one or more questions. The questions may be multiple choice questions (e.g., with 5 answers). The assessment may be scorable based on the answers provided by the user. For example, the user's score may increase by 1 for every choice 'A' marked, by 2 for every choice 'B' marked, etc.

In various embodiments, the assessment may not be clinical or strictly clinical. In various embodiments, a user may complete an assessment related to the bond established between the user and the provider. In various embodiments, a user may complete an assessment related to their attitudes in the workplace. As will be appreciated, various embodiments contemplate that other assessments and/or other types of assessments may be completed by the user.

At step 1228, a completed assessment is received from the user. In various embodiments, the user may participate in multiple assessments over the course of receiving services (e.g., receiving treatment). In various embodiments, the user completes the same assessment repeatedly at different times. In this way, the user's progression towards improvement (e.g., improvement in clinical symptoms) may be tracked over time.

At step 1230, the user may provide various types of feedback. Such feedback may include how easy it is to use the platform, how effective the received services have been, how much they like their provider, suggestions to improve the system, and/or any other feedback. Feedback may be provided in the form of a survey, via freeform text, or via any other method.

At step 1235, the user may switch providers. For example, the user may indicate that they wish to experience treatment using a different style, and may therefore request to try a different provider. Then, for example, the user may be matched with a provider again as described above.

At step 1240, the user may receive a notification from the platform. Thus, the notification may not originate from the user's provider. The notification may indicate that a new article of potential interest has been posted to a blog associated with the platform, that a new feature has been added to the platform, that a user's next payment is due soon, that a user should try to complete an assessment within the next two days, and/or may indicate any other item of possible interest to the user.

At step 1245, the user may switch a level of services he/she is receiving (e.g., the user may switch plans).

At step 1250, the user's account status may change. An account status may change if the user desires to take a break from treatment while not ceasing treatment, in which case the account may enter a 'freeze' status. An account status may change if a user has not kept current with payments due. An account status may change if the user indicates a desire to stop treatment in the future (e.g., at the end of the current payment cycle). An account status may change if the user indicates a desire to stop treatment immediately. An account status may also change when a user resumes treatment (e.g., after a break), or when a user catches up on payments. Various embodiments contemplate other reasons for which a user's account status may change.

The registration process for a user may be facilitated in various ways. In some embodiments, a live person interacts with the user (e.g., via interactive electronic chat). The live person may ask the user questions in order to obtain data on the user (e.g., the user's name, age, state or residence, etc.). The live person may field questions from the user and provide pertinent information to the user (e.g., what to expect from a provider).

In some embodiments, a user interacts with an automated program associated with the platform (e.g., with a chatbot). The program may ask the user various questions, including asking new questions depending on answers received for earlier questions. Once sufficient information from the user has been gathered, the automated program may trigger a matching algorithm to select a provider (or set of candidate providers) to match with the user.

In various embodiments, a user may register by populating fields on a static or interactive web page, by going through screens of an app (e.g., an Android or iOS app), by speaking to a customer service representative over the phone, or via any other means.

Figure 13:
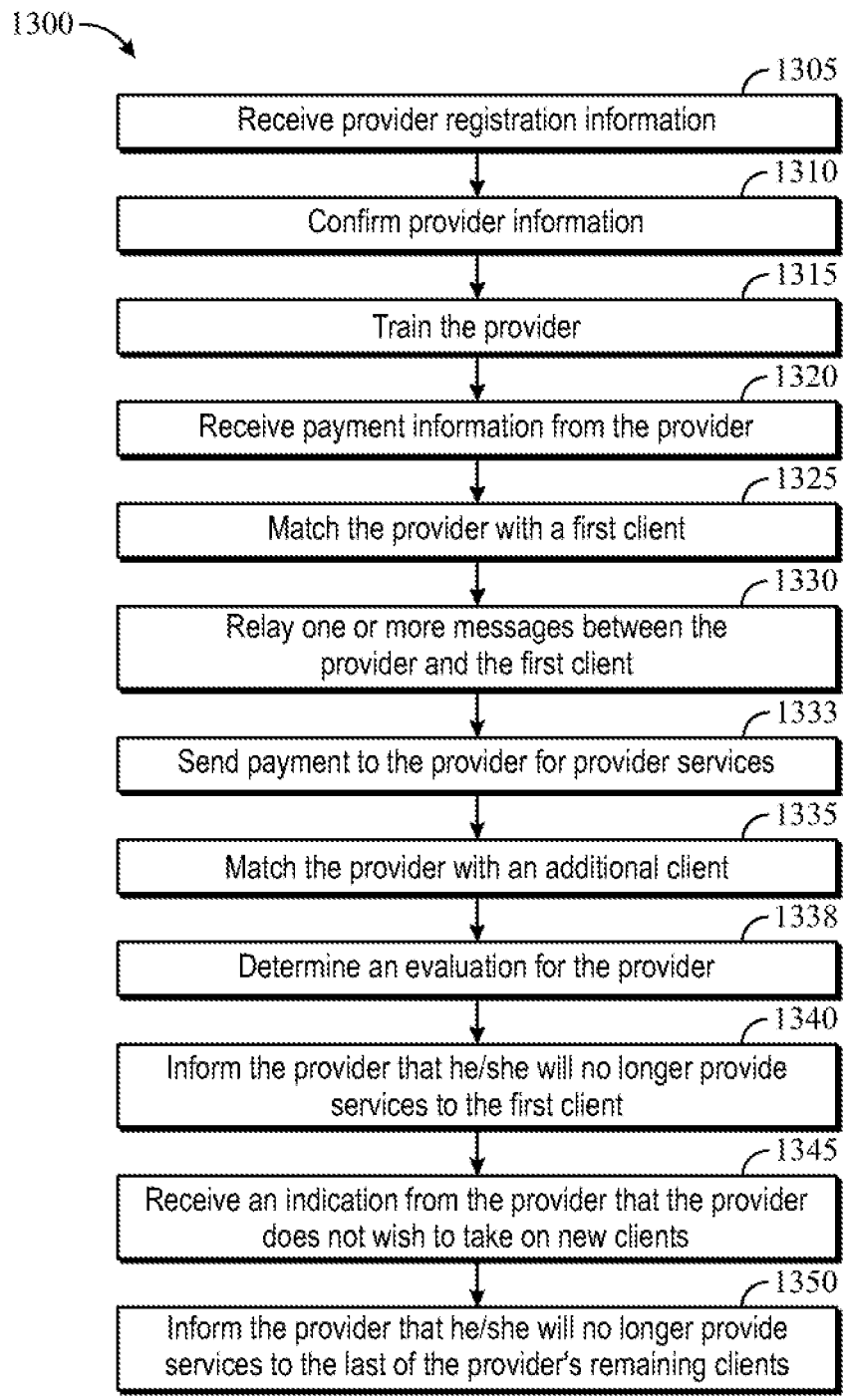
FIG. 13 shows a flow diagram of a provider's interaction with a system according to some embodiments.

With reference to FIG. 13, an exemplary provider process flow 1300 is shown according to some embodiments.

At step 1305, the provider registers with the platform. The provider may create a username and password and provide one or more items of information, including a name, address, state, country, location, city, specialty, years of experience, name of any current business (e.g., name of a clinic or practice with which the provider is associated), credentials, licensing information, geographic regions (e.g., states, countries, etc.) in which the provider is licensed to provide services, schools attended, degrees earned, areas of expertise, preferred methods or techniques for providing services (e.g., cognitive behavioral therapy) desired number of clients, maximum number of clients that can be handled, dates of availability, times of availability, and any other pertinent information.

At step 1310, the platform may confirm one or more items of information given by the provider. For example, the platform may confirm the provider's licensing information, years of experience, and/or degrees. The platform may, for example, contact licensing authorities, contact universities, contact professional organizations, et. In various embodiments, the platform may check for any outstanding complaints or actions against the provider. In various embodiments, if the platform is able to confirm information given by the provider, and has found the provider to otherwise be in good standing, then the platform may permit the provider to proceed with onboarding.

At step 1315, the provider may engage in training. Training may include techniques for adapting the provider's existing skills and practices to the online world. Training may include working with other (e.g., senior, experienced) providers. Training may include reading training literature, watching training videos (e.g., on lesson.ly), engaging in mock situations of providing services, and/or any other training scenario.

At step 1320, the provider may provide payment information. The payment information may include a bank account or other financial account identifier, PayPal account, Venmo account, or any other account information. The payment information may indicate how the provider is to be paid for his/her services.

At step 1325, the provider may be matched with a first client. The client may be the first client that the provider receives since registering with the platform.

At step 1330, the provider may proceed to exchange messages with the client and may thereby proceed to provide services (e.g., therapeutic treatment) to the client. The provider may encourage the client to complete periodic assessments (e.g., clinical assessments).

At step 1333, the provider may receive payment for services. The platform may submit payment to an account (e.g., bank account) previously indicated by the provider. The provider may be paid in various other ways, as will be appreciated. In various embodiments, the platform may separately bill the provider's client. However, in various embodiments, the platform may pay the provider irrespective of whether payment is ever received from the provider's client.

At step 1335, the provider may take on an additional client. In various embodiments, the provider may work with multiple clients in parallel. The provider may be limited to a platform-defined maximum number of clients and/or may be limited to the maximum number of clients the provider has agreed to take on.

At step 1338, the provider may be given an evaluation. The evaluation may be a score, rating, ranking, or the like. The evaluation may be determined based on one or more factors. Such factors may include: an amount by which the provider's clients have improved, a rate at which the provider's clients have improved, the length of time the provider's clients have remained in treatment, the diagnosis of the provider's clients, the responsiveness of the provider (e.g., the average time to respond to clients), feedback provided by the provider's clients (e.g., about the provider, e.g., about the platform), the degree to which the provider has used different communication methods to interact with the client (e.g., the degree to which the provider has used text, video, audio, images, etc.), the provider's level of adherence to platform requests or requirements and/or any other factors.

At step 1340, the provider may lose the first client. The client may have decided he no longer needs or wants treatment. The client may have decided to try a different provider.

At step 1345, the provider may elect to stop taking new clients.

At step 1350, the provider may finish with the last of their existing clients. The provider may thereby become inactive on the platform.

The aforementioned describe processes according to some embodiments. However, various embodiments further contemplate, for any processes described herein, that one or more steps may be added, one or more steps may be omitted, steps may be performed in different orders, steps may be combined, individual steps may be broken into multiple steps, certain steps may be alternatives of one another, and/or flow may proceed in any acceptable fashion.

With reference to FIG. 14, an exemplary data structure 1400 storing user (i.e., client) information is depicted. The data structure depicted in FIG. 14, as well as within other Figures, includes various column headers (noted with reference numerals) and various rows, with a given row containing related data (e.g., data related to the same individual) and with each data element in a row corresponding to the analogous column header.

Field 1405 stores a "user id", which may represent a unique identifier assigned to each client. Fields 1410, 1415, 1420, and 1425 may store, respectively, a last name, first name, an email address, and a nickname of the user. In various embodiments, the user may select a preferred nickname. In various embodiments, a user may wish to remain anonymous, in which case the nickname may be the main or only way by which the user is addressed. Field 1430 may store a user's date of birth, or as much of a date of birth as the user has provided (e.g., the user's year of birth). In various embodiments, a user's age may be stored directly. In any case, a user's age may be determined, and may be used, for example, to ensure the user is eligible for services and/or to determine whether parental consent is required for the user to receive services.

Fields 1435 and 1440 may store, respectively, a user's start date and a user's end date with the platform. The user's start date 1435 may represent, in various embodiments, the user's first day (or day and time) on the platform, the user's first day paying for services, the user's first day engaging with the platform, or any other suitable date and/or time. The user's end date 1440 may represent, in various embodiments, the last day for which the user has paid for services, the last day that the user has engaged with the platform (e.g., sent a message), the date upon which a user has expressed an interest to cease receiving services, or any other appropriate date. Field 1445 may store a user's address, or as much of the user's address as is available. Obtaining the user's address may ensure, for example, that the platform can match the user with a provider that is eligible to (e.g., licensed to) provide services in the areas (e.g., the state) where the user resides. Field 1445 may store a user's financial account identifier. This may be used for charging the user for services. In various embodiments, any other pertinent information (e.g., bank name, routing number, credit card issuer, etc.) may be stored and/or used for obtaining payment from the user.

Field 1455 may store a user's plan information. Plan information may determine, in various embodiments, what services the user is entitled to, how often the user is to be billed, or any other pertinent information.

Field 1460 may store a user's stated preferences as to what he/she is looking for in a provider. For example, a user may state that he/she prefers an older provider, a provider of a particular gender, a provider that speaks a particular language, etc. This information may be used in an attempt to match a user with a suitable or most suitable provider.

Field 1465 may store information about the last payment received from the user. In various embodiments, a more detailed payment history may be stored (e.g., a history of all payments made by a user may be stored). By comparing field 1465 with the present date, it may be determined whether the user is current with his payments, whether another payment should be charged to the user automatically, whether the user's account should be 'suspended' or 'frozen' pending receipt of payment, whether the user should be contacted by customer service, or any other appropriate action.

Fields 1470 and 1475 may store, respectively, a user's login name and password. These may be required for accessing the platform (e.g., via app; e.g., via web page), including accessing a user's running conversation with his provider. In various embodiments, further authentication may be required to access the platform, such as a two-factor authentication, or any other type of authentication.

Field 1480 may store emergency contact information for the user. This may represent, for example, contact information of a friend or relative. It may be utilized if a provider determines that a user is in danger, or is a danger to another, for example.

Though not shown explicitly data structure 1400 may store other fields as well, such as a user's gender.

Figure 15:
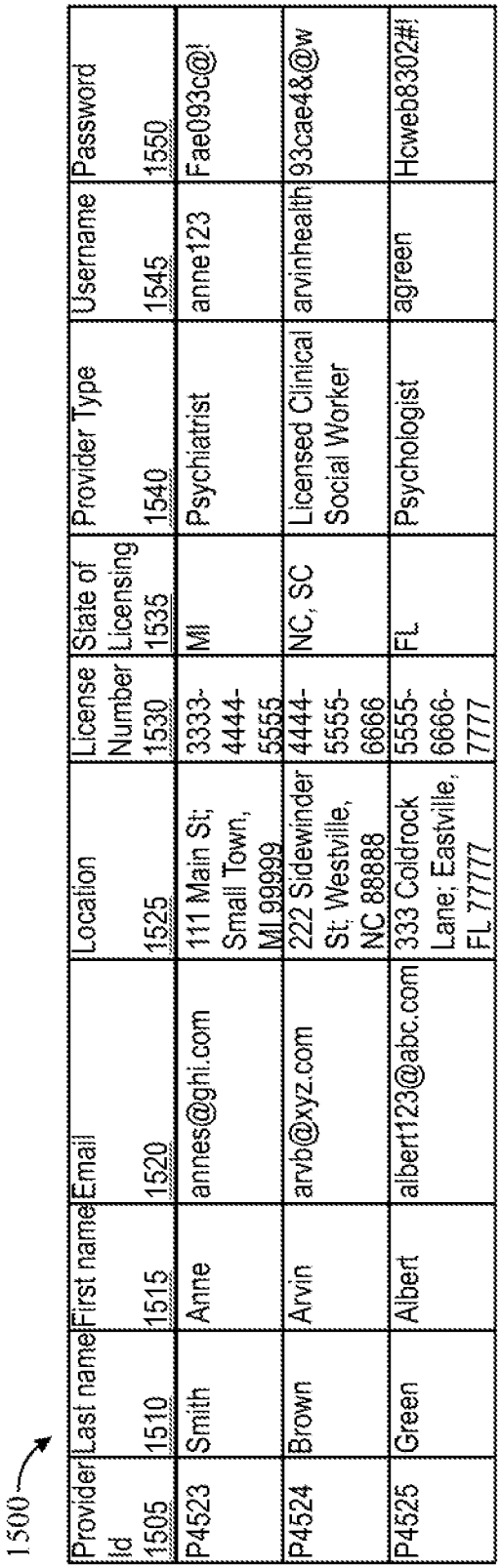
FIG. 15 shows a data structure storing provider information according to some embodiments.

With reference to FIG. 15, an exemplary data structure 1500 storing provider information is depicted. Field 1505 stores a "provider id", which may represent a unique identifier assigned to each provider. Fields 1510, 1515, 1520, may store, respectively, a last name, first name, and email address of the provider. Field 1525 may store the location of the provider. The location may represent, in various embodiments, the address of the provider's business or practice, the provider's residence address, or any other address of the provider. Field 1530 may store the provider's license number or any other licensing, accreditation or other professional information. Field 1535 may store the provider's location (e.g., state) of licensing or accreditation. This information may represent locations or geographies in which the provider is permitted (e.g., legally permitted) to offer services (e.g., psychotherapy services). The provider's location of licensing may be used to match the provider with suitable users (e.g., with users in a similar location or state).

Field 1540 may store the provider type. This information may indicate what types of services the provider offers (e.g., psychotherapy versus psychiatry). This information may also be useful in matching a provider with a suitable user (e.g., with a user seeking the types of services that the provider offers). In various embodiments, the types of services offered by a provider may be stored directly.

Fields 1545 and 1550 may store, respectively, a provider's login name and password. As with users, further authentication may be required, in various embodiments, in order for a provider to access the platform. Once a provider has obtained access, the provider may be able to view the provider's running conversations with users to which the provider is offering services (e.g., psychotherapy treatment).

Figure 16:
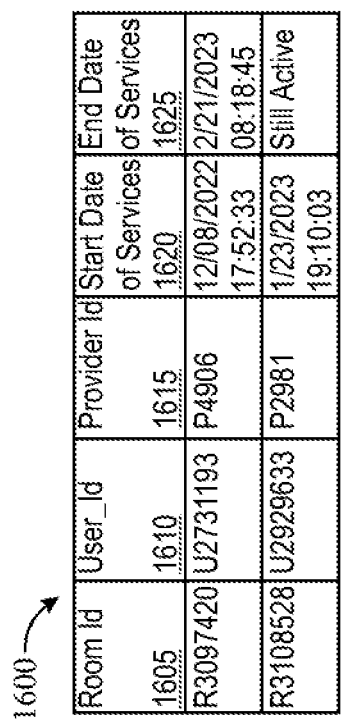
FIG. 16 shows a data structure storing information about provider and client relationships according to some embodiments.

With reference to FIG. 16, an exemplary data structure 1600 storing information about relationships between providers and clients is depicted. Each row in data structure 1600 may represent a relationship between a provider and a client such that the provider is or was providing services (e.g., psychotherapy services) to the client. These relationships may come about as the result of matching the provider with the client, as described elsewhere herein.

In various embodiments, interactions between providers and clients are said to occur in "rooms", which may be thought of as electronic or virtual analogues of physical rooms where the two parties would meet if they were meeting face-to-face (e.g., for an in-person psychotherapy session). In various embodiments, these "rooms" on the platform are accessible only to the provider and the client. Upon accessing a room, the provider and client can see the history of their conversation with one another. Other items may also be visible, in various embodiments, such as clinical notes that the provider has recorded for himself/herself, portions of a conversation that the user has highlighted or otherwise marked (e.g., "starred"), etc. In various embodiments, either the provider or the client may access the room separately, compose a message for the other party, etc. Thus, the conversation and/or interaction between the two may proceed asynchronously, and potentially without both parties ever accessing the room at the same time.

Field 1605 may store an identifier for a room in which a provider-user interaction took place. Fields 1610 and 1615 may store, respectively, identifiers for a particular user and a particular provider involved in a provider-user interaction. Fields 1620 and 1625 may store, respectively, the start date of services provided, and the end date of services provided. In some cases, a provider-user relationship may be ongoing or in process, in which case there may be no end date listed. Rather, another designator, such as "Still Active" may be listed.

In various embodiments, if a user switches providers, then the user may continue to engage with the new provider in the same room as that in which he had engaged with the old provider. In such cases, a new row may be stored in table 1600, where such new row lists the same room and user id, but lists a new provider id, and new start and end dates of services. However, in various embodiments, other methods for switching providers may be implemented, such as having both the user and the new provider engage within a new room.

Figure 17:
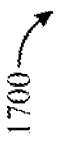
FIG. 17 shows a data structure storing information about messages according to some embodiments.

With reference to FIG. 17, an exemplary data structure 1700 storing information about messages between providers and clients is depicted. Field 1705 may store a unique message id assigned to each message. Field 1710 may store a date and time when the message was sent (or created, or received, in various embodiments). Fields 1715 and 1720 may store, respectively, identifiers for the originator and recipient of a message. In various embodiments, the originator and recipient will be either a user or a provider. In some embodiments, a message may originate from another source, e.g., a message may be an automatically system-generated message, a message from a system administrator, a message from a customer service representative, or the like. In some embodiments, a message may be destined to another source, such as to customer service. In such cases, other types of identifiers may be used to identify the originator or recipient of a message.

Field 1725 may store a message type. In various embodiments, message types may include text messages, audio messages, video messages, and/or messages comprising an image or photo. In various embodiments, text messages may include plaint text, emojis, and one or more other types of characters. Various embodiments contemplate that any other type of message may be sent as well, or that messages may be typed or classified according to some other classification scheme.

Fields 1730 and 1735 may store, respectively a character count and a word count for a message. The word count may be based, for example, on the number of contiguous blocks of characters that don't include spaces or punctuation. However, other methods of determining word count are also contemplated according to various embodiments. In various embodiments, by tracking character count and/or word count, the system may ascertain a client's level of engagement, a provider's level of engagement, whether a client and provider are exhibiting similar levels of engagement, whether a provider is meeting service level agreements, and/or any other metric or objective.

Field 1740 may store a message duration. A message duration may apply to audio or video messages. A message duration may likewise help the system to ascertain levels of engagement by clients and/or providers.

Field 1745 may store the content of messages. The messages may thereby be available to clients and providers for review each time they access the system. In various embodiments, messages are stored in encrypted form. Messages may likewise be transmitted in encrypted form. In various embodiments, messages are only decrypted on a client or provider device.

Figure 18:
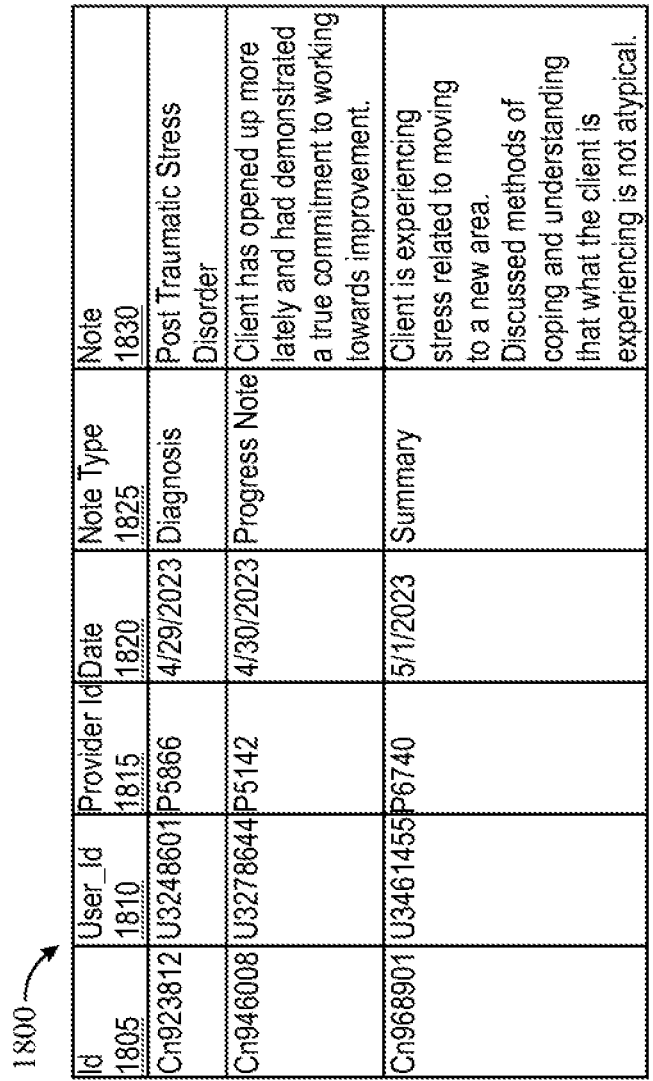
FIG. 18 shows a data structure storing clinical notes according to some embodiments.

With reference to FIG. 18, an exemplary data structure 1800 storing clinical notes is depicted. Clinical notes may represent notes that a provider keeps in order to aid with the provision of services, but which are not necessarily intended for viewing by the client. Clinical notes may help to refresh the provider's memory about what services have been provided so far, what progress has been made by a client (e.g., progress towards improvement of clinical symptoms), and what directions the provider intends to pursue going forward. In various embodiments, clinical notes may be used to satisfy reporting requirements, e.g., for insurance companies or employers paying for the provider's services. In various embodiments, clinical notes may serve as guides for new providers that may take over for existing providers, or for other providers that may provide services to the client concurrently.

Field 1805 may store a unique identifier assigned to each clinical note. Field 1810 may store an identifier of the user whom the note is about. Field 1815 may store the identifier of the provider that created the note. Field 1820 may store the date (including the time in some embodiments) when the note was made.

Field 1825 may store the note type. In various embodiments, a note type may be a "Diagnosis" whereby the provider may identify one or more conditions that the provider believes may be applicable to the client. A note type may be a "Progress Note" whereby the provider may note what progress the client has made over some period of time (e.g., over the last week, e.g., since commencement of treatment, e.g., over the past month, etc.). A note may be a "Summary" whereby the provider may summarize a client's condition, the state of treatment or any other information. The aforementioned represent some types of notes, but various embodiments contemplate that other types of notes may be used, and that notes may include other types of content.

Figure 19:
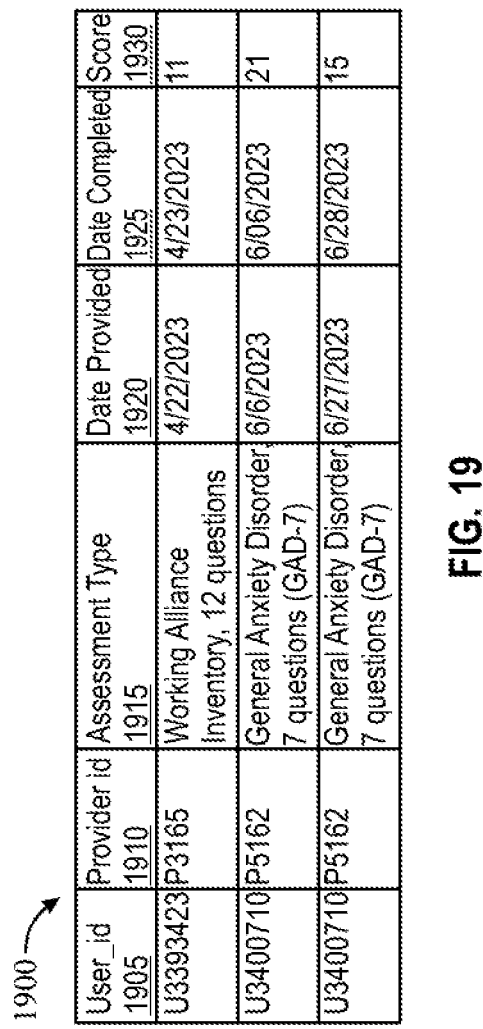
FIG. 19 shows a data structure storing assessments according to some embodiments.

With reference to FIG. 19, an exemplary data structure 1900 storing assessments is depicted. Assessments may be used to track a client's condition, a client's satisfaction with services, a client's satisfaction with his provider, or any other aspect of the client.

Field 1905 may store an identifier of a user to whom an assessment has been given. Field 1910 may store an identifier of the provider who was providing services to the user at the time the assessment was given. The provider may have been involved with providing the assessment to the user, alerting the user to complete the assessment, reviewing the results of the assessment, or involved in any other way.

Field 1915 may store an indication of the assessment type that has been given. The assessment type may be a standard type of assessment, such as on described in medical or psychological literature. Example assessments may include the General Anxiety Disorder, seven question format (GAD-7), or Working Alliance Inventory. Although not depicted explicitly herein, the system 100 may store details about each assessment, such as the individual questions, possible answer choices, scoring methodology, etc. This may allow the system to give the assessments to users, and to score results.

Field 1920 may store the date (including time in some embodiments) when an assessment was given to a user. Field 1925 may store the date (including time in some embodiments) when an assessment was completed by a user. Field 1930 may store a score that the user obtained on the assessment.

As depicted in FIG. 19, user U3400710 has received the same assessment on at least two dates (Jun. 6, 2023 and Jun. 27, 2023). The user has scored twenty-one on the earlier assessment and fifteen on the later assessment. This reveals that the user has shown an improvement in symptoms over time on this assessment (in this and some other cases, lower scores signify improvement). In various embodiments, a user may take the same assessment any number of times. The same user may also take different types of assessments.

Figure 20:
FIG. 20 shows a data structure storing feedback according to some embodiments.

With reference to FIG. 20, an exemplary data structure 2000 storing user feedback is depicted. User feedback may be obtained in various ways. These may include surveys, in-app surveys, web surveys, email surveys, app reviews, phone surveys, conversations with customer service, or any other format or modality. Feedback may represent a user's opinion about services, the platform, the user's provider, the user's experience, the user's opinion of the efficacy of services, etc.

Field 2008 stores a date (and time in some embodiments) when feedback was obtained from a user. In various embodiments, the system may also store a date when feedback was solicited from the user.

Fields 2010, 2015, 2020, 2025, 2030 store user feedback, respectively, on how easy the user found the platform to use, to what degree the receipt of services through the platform helped the user improve, how likely the user would be to recommend the platform to a friend, how knowledgeable was the user's provider, and how responsive was the user's provider. Numerical responses may represent user responses on a scale, e.g., from 1 to 5, with higher numbers being more favorable. As will be appreciated, various embodiments contemplate that users may provide feedback on other topics, and feedback may be captured in various different forms.

FIG. 20 represents user feedback in the form of numerical ratings, but in various embodiments, feedback may also take the form of words, letters (e.g., A through F), emojis (e.g., a smiling face through a sad face), emoticons, text, free-form text, or any other form.

Though FIG. 20 depicts user feedback, various embodiments contemplate that provider feedback may also be obtained and stored. Provider feedback may include feedback about the provider experience, training, helpfulness of platform resources, and any other topic or aspect of the system.

Data depicted herein does not necessarily represent consecutive or contiguous data elements, rows, objects, or the like. In various embodiments, data elements, rows, objects, or the like need not be stored in the same order as they are depicted herein. For example, rows need not be sorted by date, by id, or by any particular value.

Data structures described herein may be depicted as tables and/or database tables. However, various embodiments contemplate that data may be stored in any suitable data structure or in any suitable fashion. The aforementioned represent some data that may be stored in various embodiments. However, it will be appreciated that various embodiments contemplate the storage of additional or alternative data, including any appropriate data for use in various embodiments.

Client Engagement

Conventional indices to track customer behavior may have one or more deficiencies. Deficiencies may include one of more of: (1) difficulty making meaningful adjustments over frequent time intervals; (2) lack of methodology for setting parameters in a systematic fashion; (3) lack of normalization to reflect activity of a client relative to other 'similar' clients, e.g., an appropriate cohort such as those who have been diagnosed with the same mental health condition; (4) lack of connection to a set of possible actions to be taken by a provider and/or to an automated action taken by the web-based application itself, based on the value of the index; and (5) lack of connection to domain-specific customer actions.

Various embodiments describe measures of client engagement that address one or more aforementioned deficiencies. In various embodiments, these measures may be domain-specific, such as specific to the behavioral healthcare domain. Various embodiments describe how such a measure can be implemented within the context of a web-based computing platform that enables text, audio, and/or video-based communication between behavioral healthcare providers and their patients. However, it will be appreciated that various embodiments contemplate the use of measures described herein in other domains (e.g., in domains besides healthcare, behavioral health etc.), and on other platforms.

In various embodiments, providers (e.g., behavioral health care providers treating clients via messaging carried out on a web-based computing platform) may sometimes have difficulty gauging how engaged a client is with their treatment. Providers may have difficulty ascertaining a client's level of engagement even if the provider can see the content of client messages and/or the time client messages were sent.

Data-derived measures of engagement, such as indices that track the activity a client performs on the platform, can augment the digital therapy environment and substitute for some of the physical cues that would have been available to the provider in a face-to-face setting. Various indexes can be used to satisfy various purposes. In some embodiments, an index may provide a summary view of a client's usage of various capabilities of the platform itself, i.e. the frequency and timing of sending messages, the completion of surveys related to a client's symptoms, updating of the client's subscription to the service, requesting a transfer to a new provider, etc. In some embodiments, an index may be indicative of a client's engagement or commitment to the therapeutic process. A possible scenario might be that the client's use of platform capabilities is high at the beginning of treatment but then decreases over time, while his commitment to therapy steadily rises as measured by the language used in the messages exchanged with the therapist. Understanding correlation in the movements of the two indices over time can give the provider additional insight as to the client's engagement with his behavioral healthcare. Additionally, the provider may find it useful to compare this explicit summary with her implicit estimate of the client's engagement. If the activity index additionally includes data that is not transparently available to the provider, such as behavioral data collected by the platform, the index provides information that goes beyond what the provider knows from interacting with the client.

A client engagement index may provide a convenient summary of current and/or past activity that the provider may not necessarily keep track of explicitly. In various embodiments, a client engagement index can provide additional meaning when the index is benchmarked against index values of other clients. This could be useful, for example, to new providers on the platform, who may not have a clear idea of what a typical level of engagement is.

Various embodiments include determining a client engagement metric based on actions taken by a client. Various embodiments include determining a client engagement metric based on behavioral health-related actions taken by a client. Various embodiments include determining a client engagement metric based on behavioral health-related actions taken by a client participating in therapeutic treatment. Various embodiments include determining a client engagement metric based on behavioral health-related actions taken by a client participating in therapeutic treatment via a network-based (e.g., web-based) computing platform that enables text, audio, and/or video-based communication between behavioral healthcare providers and their patients.

Actions taken by a client might include: sharing an emotion within a text message to the provider; completing a survey measuring symptom levels; stating a situation that triggers an emotion (e.g. anxiety); completing a live video session with a therapist; completing an intake assessment; and/or any other suitable action. In various embodiments, a numerical value is associated with one or more client actions. The numerical value may indicate the relative importance of the action for measuring client engagement. In various embodiments, a summary score is calculated from these numerical values. In various embodiments, the summary score reflects an aggregate activity within a specified window of time.

In some embodiments, client activity is modeled using an impulse-decay function, where the decay is assumed to follow an exponential model. In some embodiments, client activity level is modeled as an exponentially decaying quantity $S(t)=S_0 e^{-\lambda t}$, where $S_0$ denotes an initial activity level and $S(t)$ gives the activity level after t units of time (e.g. hours). This requires a choice of decay constant $\lambda$ which can be chosen in one or more ways. Reasonable choices for $\lambda$ might include choices that result in the function $S(t)$ reaching a desired fraction of an initial value (e.g., 0.5 of an initial value) following a predetermined period of time (e.g., 1 day) with no client activity. For example, if we let $S_0=1$ and $\lambda=0.0432 \cdot h^{-1}$, then we define a process where the activity level starts at $S(t)=1$, the next interaction is expected in 24 hours on average, and after 72 hours, $S(t)=0.05$.

When the client interacts with the platform, we add some quantity (the impulse) to the activity level, $S(t)=S(t)+S_i$. We can select a value for $S_i$ such that a client interacting with the platform once every $T_0$ (e.g., 24 h) would each time have activity level restored to $S_0$ (e.g., 1.0) by simply solving $S_0 e^{-\lambda T_0}+S_i=S_0$ which gives $S_i=0.645$ when $S_0=1$, $\lambda=0.0432 \cdot h^{-1}$, $T_0=24$. We can also select a value for $S_i$ to reflect the relative weight of activity i compared to another activity. For example, we may associate an impulse value of 2.0 to the activity of sending a video message whereas a text message might have an impulse value of 1.0. Other values can be chosen in the same manner to reflect different beliefs about initial activity level, average time to the next event, etc.

Figure 27:
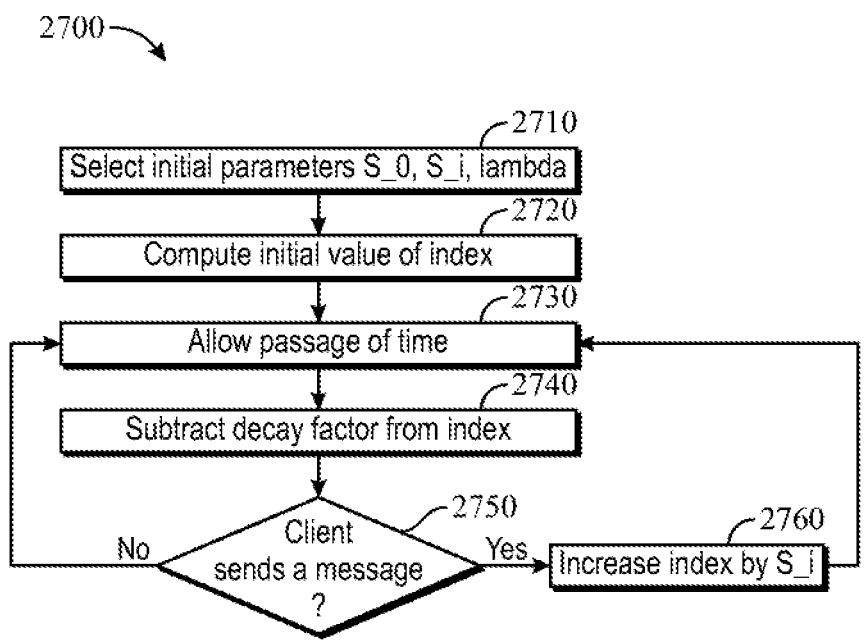
FIG. 27 shows a flow diagram of a process for determining engagement metrics according to some embodiments.

With reference to FIG. 27, an illustrative process 2700 for computing an index of a client's activity level over time is depicted. At step 2710, initial values for parameters $S_i$, $S_0$, and $\lambda$ are chosen. (e.g., $S_i=0.645$ when $S_0=1$, $\lambda=0.0432 \cdot h^{-1}$, however, other values may be chosen as well). At step 2720 an initial value of the index is computed. In various embodiments, this is simply $S_0$. However, in various embodiments, it is desired that the initial value of the index be at a particular time, such as at 12:00 midnight on the day that the client first purchased services. In such cases, the index level can be set to $S_0$ at the moment of first purchase (or of first activity) and then computed backwards in time to what it would have been at 12:00 midnight consistent with the decay function. For example, if the client's moment of first purchase is 1:00 am, we may set the activity index to be 1 at 1:00 am, which would imply that the activity index was 1.044 at 12:00 am (one hour earlier), because $1.044 * e^{-0.0432*1}=1$. In various embodiments, regardless of the time of first purchase, the initial value of the index is set to be 1 at 12:00 midnight on the day that the client first purchased services.

At step 2730, some amount of time is allowed to elapse (e.g., one hour; e.g., one day, e.g.; time until the next hour on the clock). At step 2740 a decay factor is computed based on the most recent value of the index $S_n$, the amount of elapsed time $T_n$, and the value of $\lambda$. In various embodiments, the decay factor is $S_n * (1-e^{-\lambda \cdot T_n})$. For example, with a most recent index value of 1, 1 hour of elapsed time, and $\lambda=0.0432 \cdot h^{-1}$, the decay factor would be $1*(1-e^{-0.0432*1})=0.042$. This decay factor is then subtracted from the most recent index value to get the latest index value. For example, 1−0.042 would give 0.958.

At step 2750 it is determined whether the client has sent a message during the period of time allowed to elapse at step 2730. For this purpose, the messages table 1700 may be consulted, in various embodiments.

If there has been a message, then flow proceeds to step 2760, where the value of the index is increased by $S_i$. In various embodiments, if there have been n messages during the elapsed period of time, the value of the index may be increased by $n*S_i$. Flow would then proceed back to 2730, where the passage of further time is allowed. In the event that there was no message, flow would also proceed back to step 2730, but without increasing the index.

In various embodiments, a computational benefit may be realized by using database aggregate functions to count the number of client messages that occurred during the elapsed period of time. Namely, client messages can be grouped by the time window in which they were sent (e.g., by the hour in which they were sent). An aggregate function such as COUNT can then count all the messages sent by the client within each time window (e.g., hourly period).

From step 2730, the flow may continue in a looping fashion indefinitely or as long as desired, and each subsequent value of the index may thereby be computed from the prior value.

Various embodiments contemplate that the aforementioned steps may also be accomplished in mathematically equivalent steps. For example, at step 2740, rather than subtracting a decay factor from a prior value of an index, the prior value may be multiplied by a different decay factor so as to yield an equivalent result.

More specific to the behavioral health care domain, the impulse associated with a client's activity might be given a value based on how closely the client's words match the tone of the therapist words or the similarity of the topic expressed by the client's words are to that expressed through the therapist's words. In another case, the decay rate can be a function instead of a constant, e.g. $\lambda(t)$ could define a process where the average time to next event is longer as total time since beginning therapy increases. The decay rate could also be a function of event type so that one type of event (e.g. live video) decays more slowly than another (e.g. text message).

This model reflects the fact that when a client interacts with the platform, his activity level instantly increases by some amount, because we know in that instant he is active. As time passes, the estimate of the client's activity level decreases when no further interactions occur. When the next interaction occurs, the client's activity level increases again and this time the total client's activity level is the sum of how much it increased during the second interaction and the value to which the activity level had decayed following the first interaction.

Figure 28:
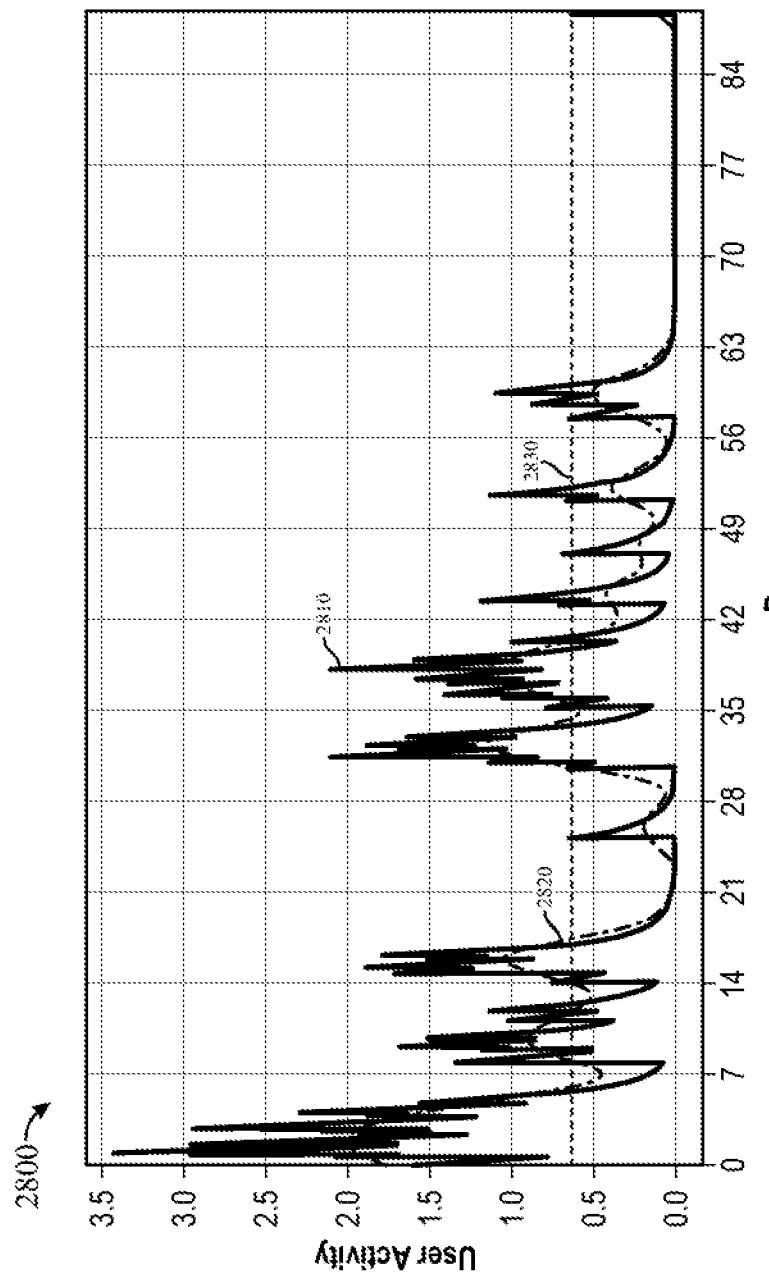
FIG. 28 shows an exemplary representation of a time evolution of an engagement metric according to some embodiments.

FIG. 28 depicts an exemplary plot of how a user activity index might change as a function of time. The horizontal axis represents the passage of time (i.e., days) and the vertical axis represents the value of the index. The jagged line represents the computed values of the activity index over time. The dashed horizontal line represents the average activity level for a user that records one interaction every 24 hours. In the first week, this client builds an activity level exceeding one, due to relatively frequent interactions. This falls to about one interaction every 24 h during the second and third weeks, then falls below this, etc.

Note that in various embodiments, the exact activity level can be aggregated to reflect the overall activity level over a specified time window, such as a day or a week. In FIG. 28, the smoothly varying line shows the activity level aggregated over a 7-day time window using a moving average smoothing method.

In various embodiments, rather than using an impulse-decay function featuring exponential decay to model client activity, a different impulse response function may be used. In some embodiments, client activity may be modeled as $S(t)=S_0*MAX(1-\lambda t,0)$, in which case, in the absence of further client activity, and for positive $\lambda$, the client activity index would decline in a linear fashion (with slope determined by $\lambda$) from $S_0$ to 0 and then remain at 0. In various embodiments, client activity may be modeled as $S(t)=S_0*1/(1+\lambda t)$, in which case, in the absence of further client activity, and for positive $\lambda$, the client activity would decay asymptotically to 0. As will be appreciated, many other impulse response functions may be used and are contemplated according to various embodiments.

In various embodiments, a model predicts, based on one or more of: (a) usage patterns, (b) the language contained in the messages exchanged between client and therapist, (c) the severity of client symptoms, what the next client action will be and/or when the next message or set of messages will occur. In various embodiments, the prediction may be made using the theory of temporal point processes. The behavior of a simple temporal point process N may, in various embodiments, be modeled by specifying its conditional intensity, $\lambda(t)$, which represents the infinitesimal rate at which events are expected to occur around a particular time t, conditional on the prior history of the point process prior to time t. In these embodiments, an estimate of the client's activity level can be formed from the inverse of the expected duration until the next client action, where the expected duration is estimated using a machine learning algorithm, such as a deep neural network algorithm.

Benchmarking Activity Level

In various embodiments, the activity index computed for a given client (e.g., for a client of interest) may be compared with one or more activity indexes computed for one or more other clients (e.g., for a cohort or reference set of other clients). This may, for example, help a provider to interpret the activity index for a client of interest in a meaningful or otherwise contextual fashion.

In various embodiments, a cohort of clients may be determined. In various embodiments, a cohort of clients with some specified quality (e.g., desirable quality) are selected. The cohort of clients may include for example, clients with the same diagnosis as a client of interest, where such clients' mental health symptoms decreased to within the 'normal' range over the course of their treatment.

In various embodiments, a cohort of clients may share one or more characteristics in common with a client of interest. Such characteristics may include: age, age range, gender, marital status, diagnosis, income, state or other geographic region of residence, language spoken, number of children, date or date range when starting treatment, plan type, and/or any other characteristic.

A cohort of clients may include a predetermined number of clients, such as 100 clients, 1000 clients, or any other chosen number. In various embodiments, a cohort of clients may include all clients meeting a set of criteria (e.g., sharing a diagnosis with the client of interest). In various embodiments, a cohort of clients may include clients whose time on the platform fell within predetermined parameters (e.g., the cohort of clients may include clients who began treatment within the last year).

Once a cohort of clients has been determined, in various embodiments, a respective engagement index may be computed for each client in the cohort. Thus, for example, if there are 100 clients in the cohort, then 100 separate engagement indexes may be determined. As will be appreciated, each individual engagement index may include multiple values, representing the evolution of the engagement index over time. For example, for the client identified by U2834976, the engagement index may take on the value of 78.3 at 1:00 pm on Dec. 5, 2023, the value of 78.1 at 2:00 pm on Dec. 5, 2023, and so on.

In various embodiments, a first client's level of activity or engagement is expressed not simply as a predetermined function of the first client's own activity, but rather as a function of the first client's own activity level in relation to the activity or engagement of the cohort of clients. In various embodiments, a reference value is computed based on the cohort of clients. Separately, the first client's engagement level is determined based only the first client's activity. Then, the first client's engagement index is computed based on the first client's engagement level and the reference value. For example, the client's engagement index may be determined to be the percentage of the reference value that is represented by the client's engagement level. For example, if the client's engagement level is 60 and the reference value is 50, then the client's engagement index may be expressed as 120% (i.e., the client's engagement level of 60 is 120% of the reference value 50).

In various embodiments, a reference value can be computed through application of an appropriate summary measure to the distribution of engagement index values for all clients in a cohort. For example, each client's engagement index value at time t in treatment might be compared to the mean or the median of the index values of the cohort clients at time t and/or the amplitude of the client's engagement index value might be scaled to reflect the typical variability in the values across the cohort at time t using, e.g. the standard deviation of cohort values or the difference between the 75th percentile and 25th percentile of the cohort values at the specified time in treatment. This will result in each new client's engagement level being comparable to the activity level of clients whose relationships with their provider results in clinical improvement in their condition, with values above zero indicating greater activity than that typically exemplified by the cohort and values below zero indicating less activity. While the individual activity levels can be computed in continuous time, the benchmarking levels are obtained by determining the aggregate value of the cohort at regular discrete intervals. For example, the end of every hour, or the end of every day, as described in the System Implementation section below.

Example

FIG. 21 shows an illustrative example of computing and storing client activity index values. Table 2100 stores various events relevant to a client activity index.

Field 2105 may store identifiers (e.g., unique identifiers) for different events. Field 2108 may store identifiers for users to which the event pertains, and for which an activity index value is being computed. Field 2110 stores the time of an event.

Field 2115 stores an event type. An event type may be "Begin treatment", which may signify the computation of an initial value of an index, as describe at step 2720. An event type of "Hourly Snapshot" or the like may signify a point in time for which we desire to compute an index value. E.g., the point in time may be a time that is exactly on the hour, exactly on the half hour, exactly at midnight etc. Having regularly spaced computation of an index value may make it easy to graph an index over time, to visualize an index over time, etc. An event type of "Message" or the like may trigger recomputation of the index because a message may represent some type of client activity or engagement. Thus, it would be an opportunity to at least partially increase the index. Other event types may include "Assessment", "Video Call", etc., and such events may, in various embodiments, signify client activity as well.

Field 2120 may store an elapsed time since the prior event. This may be used in computing a decay factor (see FIG. 27). Field 2125 may store a score (or index value) immediately before the present event. This score may be based on a score following the most recently prior event (see Field 2135) minus a decay factor.

Field 2130 may store a score increase (e.g., an increase in an index value) associated with each event. In various embodiments, different types of events, even if they all represent client activity, may increase the index by different amounts. For example, event E38292095 has led to a jump in the index value (i.e., a score increase) of 1.29, which is twice the jump corresponding to E38292025, when a "Message" event occurred. In various embodiments, hourly snapshots do not lead to any increase in the index value. They are merely there to compute an index value at a desired time.

Field 2135 may store a score (e.g., an index value) immediately following an event.

As will be evident, FIG. 21 assumes the recomputation of an index value following every event. This has the advantage of accurately maintaining an up-to-date an exact index value. On the other hand, some speed may be sacrificed, in some embodiments, when compared to embodiments where events are first aggregated over some period of time (e.g., counted), and then a score or index is updated based on the count of events.

Augmenting a View of Activity Level

Various embodiments include determining and depicting a metric of client activity level over time. A depiction may take the form of a graph or plot. In various embodiments, the plot may be augmented with additional information. In various embodiments, the additional information may include examples or summaries of client activity (e.g., client messages) that led to the depicted activity level in the plot.

In various embodiments, when the client sends a message, the client's activity metric will increase, and this increase may be visible as a spike or upwards trend on a plot of the client's activity metric over time. In various embodiments, the plot may be augmented with a word or set of words from the client's message. For example, suppose a client's message reads, "I felt empowered once I started putting myself in other people's shoes." In various embodiments, a keyword (e.g., "empowered") may be extracted from the client's message (e.g., via natural language summarization methods), and the keyword may be displayed on the plot in proximity to the spike in the client's activity level. In this way, a provider may quickly peruse the graph, note where activity levels increased, and get a quick summary of what was causing or happening as the activity level increased.

In various embodiments, if a client sent a message with an image, then the plot may include a representation of the image (e.g., a compressed version, e.g., a thumbnail, e.g., the original image). The plot may include the representation in proximity to the plotted spike or increase in activity level. In various embodiments, if the client sent a video message, one or more frames from the video message may be used to augment the plot.

In various embodiments, a plot may show a representation of a message such as summary text or a thumbnail image. In various embodiments, if a provider wishes to delve deeper, the full message, full image, and/or full video may become visible. For example, the provider may touch or hover his mouse over a message summary on the plot in order to see the full message.

In various embodiments, the plot may be annotated with indications of significant events or dates. For example, a plot may show a date when a client lost a relative, when a client got a promotion, etc. Significant dates may also include holidays, the client's birthday, the client's anniversary, etc. The plot may also be annotated with dates that a provider deems significant, such as a time when the client made a breakthrough in their thinking, their willingness to embrace a new method of treatment, etc. In this way, for example, a client's activity level may be related to significant dates or events.

Figure 29:
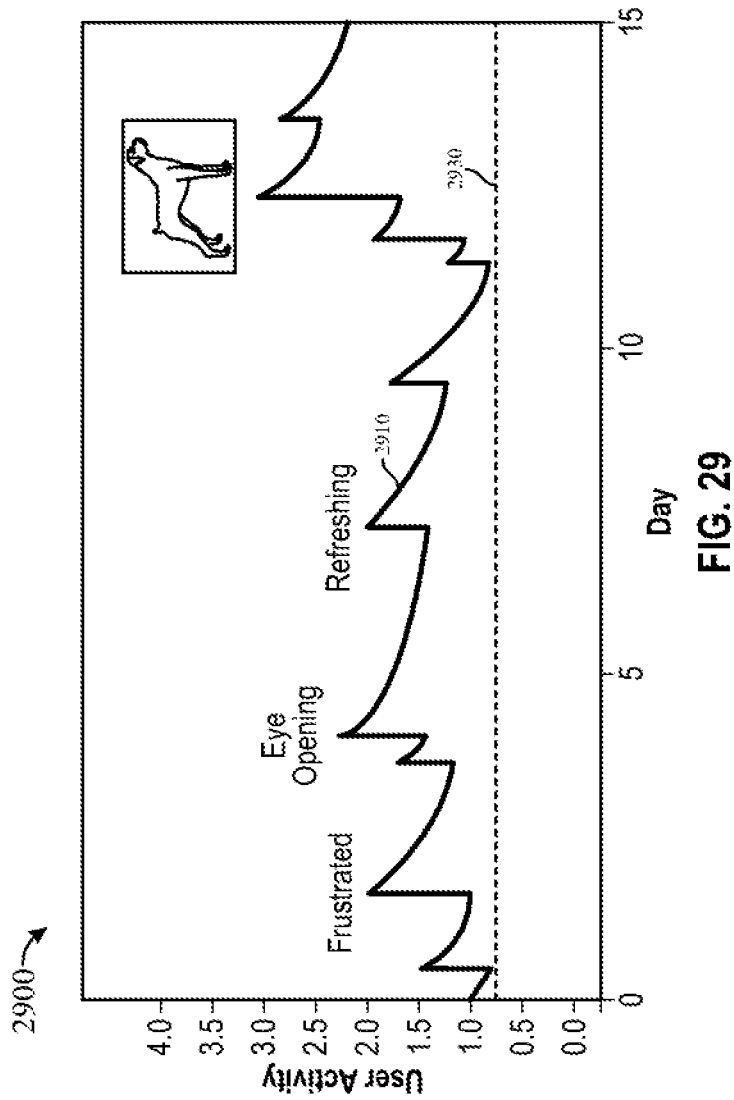
FIG. 29 shows an exemplary representation of a time evolution of an engagement metric according to some embodiments.

FIG. 29 depicts an exemplary plot 2900 of client activity level over time. The time-varying line 2910 depicts the activity level itself. At certain times, there is visible a spike in the client's activity level, which may be due to client messages. In association with certain client messages, key words have been extracted and displayed next the resultant spike in client activity levels. Also depicted is a thumbnail of an image from another one of the client's messages. The line 2930 may show, for example, an average level of engagement for a client who messages once per day.

In various embodiments, summaries or other extracts of a provider's messages may also be depicted on the plot. Even though the plot may measure a client's level of activity, showing summaries of provider's messages or other provider activity may provide an indication of what might have caused or inspired an increase in a client's level of activity.

In various embodiments, a plot of client activity level over time may show the client's assessment scores. In this way, for example, a client's activity level may be related to the client's symptom levels and/or the client's progress towards improving symptoms.

In various embodiments, a plot of client activity level over time may show dates when a client has made a payment and/or dates when a client's payment is due. In various embodiments, other significant dates in relation to a client's account may be shown. For example, a plot may show the monthly anniversaries of the client's commencement of receiving services. In various embodiments, a client's level of engagement may be related to how much remaining time is available to a client (e.g., the remaining time that a client has paid for). For example, if a client only has a day of services remaining, then a reduction in client activity level may provide some indication that the client does not intend to renew services.

Relative Levels of Client and Provider Activity Levels

In various embodiments, a level of client engagement may be depicted, not as an absolute level, but as a level relative to a provider's engagement. For example, suppose the client has been writing three messages per day and the provider has been writing two messages per day. Then, the client's engagement level may be represented as 150%, i.e., 150% of the provider's engagement level. By depicting a client's level of engagement relative to the provider's level of engagement, it may be ascertained, for example, whether a client is being appropriately responsive to the provider.

Triggering Actions Based on the Client's Activity Index Value

Beyond simply providing the healthcare provider information on how their client's engagement compares to that of a specified cohort over time, the index can be used to trigger certain treatment-related actions to occur through the web-based computing platform when the value of the client's score exceeds a specified threshold, where such actions might include recommending to the client that he use a coping skill, such as meditation, mindfulness, yoga, etc., recommending to the client that he join a peer support group, recommending to the provider that she ask an open-ended question to the client, etc.

In various embodiments, a provider may have a global view (e.g., a dashboard view) of all his/her currently active clients. See, e.g., FIG. 11. These clients may be presented, for example, as a vertical list containing the clients' nicknames.

In various embodiments, a provider's list of clients may be reordered based on changes in an engagement index for one or more of the provider's clients. In various embodiments, if a particular client's engagement index falls below a predetermined threshold, then the client may be moved to the top of the provider's list. In various embodiments, a provider's list of clients may be ordered by the value of the provider's clients' engagement indexes (e.g., they may be ordered with clients having the lowest index values towards the top of the list, and clients having the highest index values towards the bottom of the list).

In various embodiments, a provider may be barred from interacting with one or more clients based on the engagement index of a given client. For example, if a given client's engagement index falls below a predetermined threshold, the provider may be barred from messaging other clients until the provider has messaged the given clients. In this way, the provider may be forced to prioritize clients needing the most immediate attention. In various embodiments, if a provider is barred from messaging a client, then the client may be shown grayed out or with a "lock" icon on the provider's list of active clients.

In various embodiments, one or more other features of the platform may be locked or made unavailable to a provider until the provider interacts with (e.g., sends a message to) a client whose engagement index meets certain criteria (e.g., has fallen below a predetermined threshold).

Implementation

The following section describes, according to various embodiments, implementations of the client engagement score, with reference distribution and triggering of actions based on the value of the score relative to the reference distributions. Such embodiments may occur within a web-based computing platform enabling text, audio, and/or video-based communication between providers (e.g., psychotherapists) and their patients.

Figure 30:
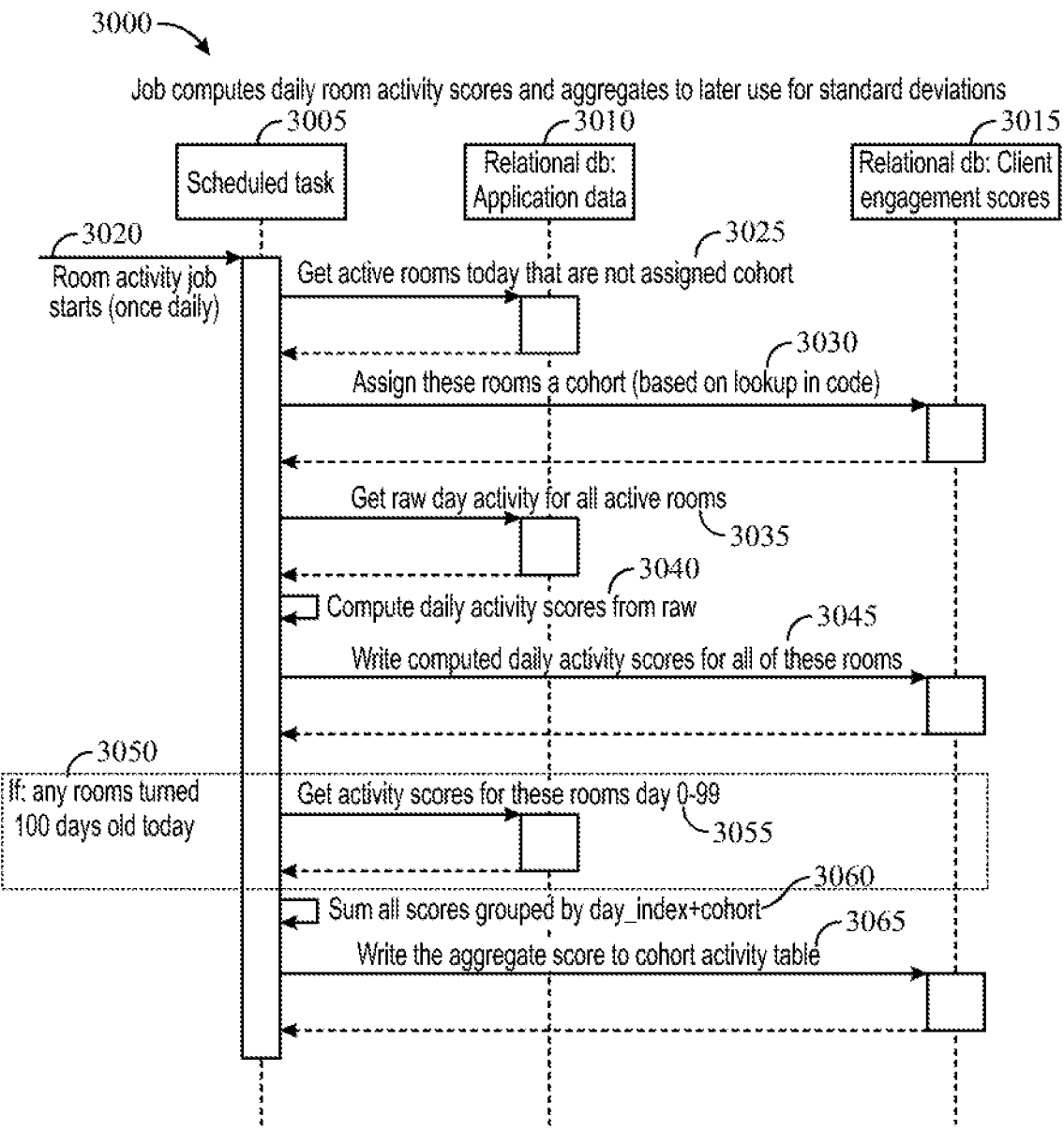
FIG. 30 shows a diagram of a process and architecture for determining engagement metrics according to some embodiments.

FIG. 30 illustrates an exemplary workflow that employs a compute server separate from the server running the web-based computing platform itself to extract all of the necessary client activity and attribute data from a replica of the primary database that stores all information collected through the platform and compute, using the method outlined in the previous section, the client engagement score for each client using the platform, determine the client cohort, and compare the score of a specific client to the typical score for his determined cohort. This score is computed each day that the client is in treatment and these scores and associated information are stored in a set of tables in the primary database. These individual scores, cohort reference values, and associated trigger thresholds can then be retrieved by the platform for, e.g. creating a graphical display of the information for the provider or determining the difference between a client's individual score and the associated cohort reference score and comparing to a threshold in order to determine whether an action should be carried out through the platform.

Figure 22:
FIG. 22 shows a data structure storing categories for cohorts of users according to some embodiments.

With reference to FIG. 22, a table 2200 storing categories of cohorts is depicted, according to some embodiments. Cohorts may represent sets of users with one or more trains in common. This may include age, gender, or condition. In various embodiments, a cohort may be defined based on any characteristic or set of characteristics of constituent clients, of providers working with the constituent clients, or based on any other characteristic, or defined in any other fashion. In various embodiments, cohorts may have constituents selected at random. Field 2205 may store an identifier (e.g., unique) for each cohort. Field 2210 may store a description of the cohort. Field 2215 may store a date (e.g., and time) when the cohort was created.

Figure 23:
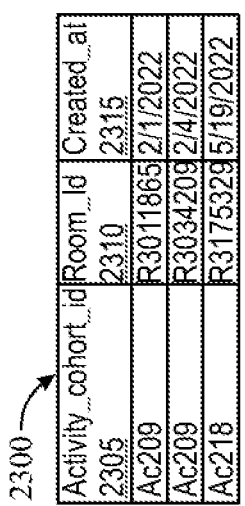
FIG. 23 shows a data structure storing assignments to cohorts according to some embodiments.

With reference to FIG. 23, a table 2300 storing assignments to cohorts is depicted, according to some embodiments. Field 2305 may store the unique identifier of the cohort to which a given client (or equivalently the given client's room) has been assigned. Field 2310 may store the room id of the room (or equivalently the user in the room) which has been assigned to the cohort listed in field 2305. Field 2315 may store the date when the assignment was made.

Figure 24:
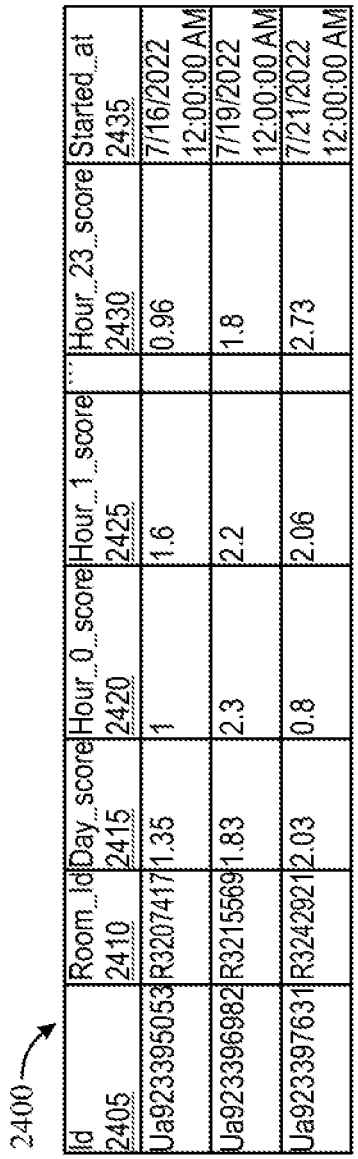
FIG. 24 shows a data structure storing engagement metrics according to some embodiments.
Figure 26:
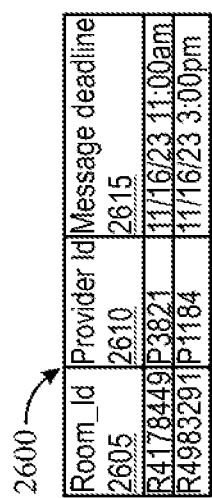
FIG. 26 shows a data structure storing message deadlines according to some embodiments.

With reference to FIG. 24, a table 2400 storing values of a client's activity index at different hours during the day is depicted, according to some embodiments. Field 2405 stores an id (e.g., unique) for each record. Field 2405 stores the room id for which the activity index values are computed. Field 2415 stores the day score, which may represent the mean or average of the scores for the given room for the given day. Note, in various embodiments, other summary metrics may be stored, such as a maximum value for the day, median value for the day, etc.

Fields 2420 to 2430 store hourly scores, beginning with hour 0 (e.g., the hour running from midnight to 1:00 am), and ending with hour 23 (e.g., the hour running from 11:00 pm to midnight the next day). As will be appreciated, there may be 24 such fields, though not all are explicitly depicted for the sake of brevity.

Field 2435 may store the date for which the hourly index values are computed.

With reference to FIG. 25, a table 2500 storing cohort metrics is depicted, according to some embodiments. Field 2505 stores an id (e.g., unique) for each record. Field 2510 stores the identifier for the cohort for which the cohort metrics are being stored. Field 2515 stores the cohort day index. For each user assigned to the cohort, the score of the user that is counted is the score that happened X many days into the services they were receiving. For example, if the cohort day index has the value of 2, then the cohort metrics will account for all cohort members scores when the members where in their second day of receiving treatment.

It should be appreciated that a cohort metric will likely aggregate over constituent member index values from different calendar days, because the constituent members may have started receiving services on different dates. I.e., Bob's second day of receiving services may have been on Jul. 9, 2022, whereas Sue's second day of receiving services may have been on Aug. 1, 2022. However, Bob's activity index value for July 9, and Sue's activity index value for August first will both be aggregated together for computation of cohort metrics corresponding to a cohort day index of 2.

As depicted in FIG. 25, metrics may be calculated for the same cohort, but over multiple days (e.g., over days 1-99).

Field 2520 may store the sum of activity scores for the constituent members of a cohort. Field 2525 may store the count of members of a cohort. Field 2530 may store the sum of the squares of activity scores for the constituent members of a cohort. The three metrics described in FIG. 25 may be sufficient for calculating mean or average activity levels for a cohort (i.e., average equals cohort sum divided by cohort count), and also a standard deviation of activity levels across a cohort. The variance can be obtained by subtracting the square of the mean activity level from the sum of the squares of the activity scores. The standard deviation is then the square root of the variance.

With the mean and standard deviation of a cohort's activity level known, and assuming a normal distribution of activity levels (or some other appropriate statistical distribution) each individual's percentile, or approximate percentile may be calculated (e.g., using a cumulative distribution function for a gaussian normal curve). In this way, a user's activity level can be shown relative to that of the members of his/her cohort, rather than as an absolute index value (which may have little or no independent meaning to the user, in some embodiments).

Though not shown explicitly, additional fields may show a date on which cohort metrics were computed, and a date on which such metrics were updated. Note that, in various embodiments, the metrics for a given cohort on a given cohort day index may change over time as new users join the cohort.

With reference to FIG. 30, a process and architecture 3000 is shown for obtaining cohort metrics. Scheduler task 3005 may represent a stored program, script, or the like that orchestrates the process, according to some embodiments. Database 3010 may store application data and may correspond, for example, to a database in replica server 213. Database 3015 may store client engagement scores (e.g., indexes) and may correspond, for example, to compute server 216.

At step 3020, the process, deemed "room activity job" starts. The process may be scheduled to start automatically on a periodic basis, e.g., once per day. At step 3025, the job gets active rooms from the current day that are not assigned to a cohort. Active rooms may be obtained, for example, from table 1600, and include rooms where there is no "End Date of Services". In various embodiments, if the job is being run for a day in the past, it may suffice to obtain rooms where the "End Date of Services" is after (and possibly on) the day of interest.

At step 3030, the rooms are assigned to a cohort. Each cohort may have one or more defining characteristics, as described above. For example, rooms in a cohort may have users with the same condition or of the same gender. Users meeting the criteria for being included in a given cohort may be found by reference to data structure 1400, for example, which may store one or more user characteristics such as age, gender, etc. Other information about a user may be found, for example, in data structure 1800, which may include a user's diagnosis or other information about the user. The users corresponding to any given room may be found by reference to data structure 1600. Through reference to and/or association of one or more of the aforementioned data structures, sufficient user characteristics, information, or the like may be ascertained to assign the user to a cohort. As will be appreciated, user information or other information may be obtained from other data structures and/or combinations of data structures.

At step 3035, the job gets raw day activity for active rooms. In various embodiments, this may be for all active rooms. In various embodiments, this may be for a subset of active rooms. The raw activity may be obtained as described elsewhere herein, such as by obtaining the times of messages, the times when a user filled out an assessment, and the like.

At step 3040, the job may compute the daily activity scores (e.g., the activity index values) activity from the raw activity.

To update the index value at each time t, the most recent value, $S(t-1)$, can be retrieved from the table activity_room_daily. The new value is then computed as $S(t)=e^{-\lambda} \cdot S(t-1)+S_i \cdot N(t)$, where $N(t)$ is the number of distinct events that occurred since $t-1$.

For the implementation, two different time intervals are defined: one is the actual time resolution of the function (i.e. the units of t), and the other is the computation interval, $f$, $f>t$. The activity levels will be computed by a job that runs every $f$ minutes/hours. When the job runs at time $t_n$, having last run at time $t_{n-1}=t_n-f$, it needs access to $S(t_{n-1})$ and a set of records for every event that has occurred since the last update, $\{\tau | t_{n-1} < \tau \leq t_n\}$. Values for $S(\tau)$ are computed and written to the table. As an example, t might be defined as hours and $f$ defined as days.

At step 3045, the computed daily activity scores are written to storage (e.g., to data structure 2400).

At step 3050, the job may determine if any rooms for which activity scores have been computed turned 100 days old today (e.g., on the day when the job is run). In various embodiments, some other threshold of days may be used. In various embodiments, all rooms may be used, regardless of the age of the room.

In various embodiments, for rooms that turn 100 days old on the current day, activity scores for only the first 100 days are obtained. In various embodiments activity scores for only the first N days may be obtained, where N is some other number (e.g., N=50, e.g., N=99).

In various embodiments, rooms are assigned to a cohort only if the rooms have been active for some minimum period of time (e.g., for 100 days). This may ensure that a given cohort contains the same number of rooms for each cohort index less than 100 days (or less than the minimum required period of time for a room to be around before inclusion in a cohort). This may also ensure that rooms in a cohort represent a sample of users that are relatively long-lived or that otherwise may serve as a good basis for comparison.

In various embodiments, a room is assigned to a cohort only once it reaches a certain age (e.g., 100 days). Additionally, room activity levels are only obtained for the room for days in which it was less than the certain age (e.g., for days in which the room was less than 100 days old; e.g. for days when the room was between 0 and 99 days old). As such, once a room is assigned to a cohort, all the information for the room that is to be included in the cohort information will already be available (i.e., will already be in the past). Thus, in various embodiments, for any given room, the activity scores from that room for inclusion in the aggregated cohort scores need only be obtained once. And these can be obtained on the day when the room reaches the critical age (e.g., 100 days). However, in various embodiments, the activity scores for a given room may be obtained some period of time after it reaches the critical age (e.g., at 102 days, etc.).

At step 3055, in various embodiments, all scores obtained for a given cohort and day index are summed. In various embodiments, the squares of all scores obtained for a given cohort and day index are summed. The resultant sums may be stored in data structure 2500. Similarly, an updated count of constituent cohort members may be added to data structure 2500.

Advantageously, cohort sum 2520, cohort count 2525, and cohort squared sum 2530 fields can be updated for each new room added to the cohort without having to access the activity index values for rooms that had hitherto been included in the fields. Namely, for example, cohort sum 2520 can be updated by simply adding to it the activity index value of a new room to be included, without worrying about what individual rooms' activity indexes had previously been summed to obtain the existing value of cohort sum 2520.

At step 3060, updated values for cohort sum 2520, cohort count 2525, and cohort squared sum 2530 are written to cohort activity table (e.g., data structure 2500).

It will be appreciated that the description and examples described herein represent some embodiments, but that contemplated embodiments are not limited to the descriptions, examples, and implementations described herein. For example, various embodiments contemplate the use of additional or alternative client activities, cohort definitions, time windows, mathematical functions, computable functions, system architectures, data structures, modes of communication, and so on.

Matching Users and Providers

Various embodiments include algorithms matching a user with a provider (e.g., with a therapist) for the receipt of provider services (e.g., for receipt of online psychotherapy).

Various embodiments include methods for ranking a list of known providers (e.g., therapists) by degree of suitability (e.g., degree of fit) for a particular user, based on at least one or more of (1) user inputs and (2) previous engagement by the provider with other users (e.g., with similar users). In various embodiments, a provider or providers which are most highly ranked for a given user may be "matched" with the user, e.g., may be selected as candidates to provide services to the user. Various embodiments use one or more criteria, including: provider field of expertise (e.g., psychotherapy expertise), provider language spoken (e.g., provider language spoken relative to the user's language spoken), provider gender, and provider license state. In various embodiments, ranking criteria may include one or more of a user's age, user's gender, user's psychological condition and user's marital status. Various embodiments may generate a list of providers (e.g., therapists) to filtered and ranked by degree of appropriateness or fit for a particular user.

In various embodiments, users may benefit from services provided (e.g., from psychotherapy treatment) where there is an intimate and/or open relationship between the customer (patient) and the provider (e.g., care giver, e.g., Psychologist, Psychiatrist, Licensed Clinical Social Worker, etc.). Where services that have traditionally be provided in a face-to-face setting are transferred into a different medium (e.g., the internet) new challenges of establishing an intimate connection between the two sides may arise.

By finding a suitable provider (e.g., a best-fit provider, e.g., a best-fit therapist) for a given customer, an intimate connection may be more likely to be established between the two sides. Taking into account the potential for short-lasting connections of users with products on the internet, a suitable provider (e.g., a best-fit provider, e.g., a best-fit therapist) may advantageously incorporate his availability to engage with the client immediately if the client were to be matched with the provider.

In various embodiments, provision of online services (e.g., therapy) enables the use of structured historical data on other customers to help determine a fit (e.g., a best-fit) of any given customer with a provider (e.g., with the most suitable available provider; e.g., with the most suitable available therapist).

An objective according to various embodiments is to find a suitable (e.g., best-fit) and available provider (e.g., therapist) for a given customer. In various embodiments, a degree of suitability is assumed to be based on the average longest relationship with similar customers, where "similar" is defined by one or more of: being in the same age group, having the same marital status, marked as having the same condition (e.g., psychotherapeutic condition) and being of the same gender.

In various embodiments, a process for finding suitable providers may consist of two phases: filtering and then ranking.

In the filtering phase, the system may use inputs about the type of provider (e.g., therapist), such as: gender, language, fields of expertise and whether the provider's state or state of licensing should match with the customer's state. Using these inputs, the system may narrow down the list of all providers (e.g., therapists). In various embodiments, the system may require that a provider matches all inputs (i.e., the system uses AND logic to combine the different inputs and uses the combination to filter out providers (e.g., therapists)).

In various embodiments, in the second phase, the system ranks the filtered list according to (1) parameters about the type of customer and (2) system parameters on the provider (e.g., therapist). Using such criteria as the customer's clinical condition, his age group, marital status and gender, an algorithm according to various embodiments ranks the most suitable providers (e.g., the best providers; e.g., the best therapists) who have been successful with similar clients. Success with similar clients may be defined as having had long-lasting provider-client relationships with such clients. In various embodiments, in the ranking process, the system incorporates more parameters pertaining to the provider (e.g., the therapist). Such parameters may include the availability to take a new client and how well the provider's own ranking of fields of expertise matched the fields requested in the first phase.

In various embodiments, the system uses three vectors: success with similar clients, availability to take new clients and field of expertise matching, in order to determine the ranking of the filtered list of providers (e.g., therapists).

Figure 31:
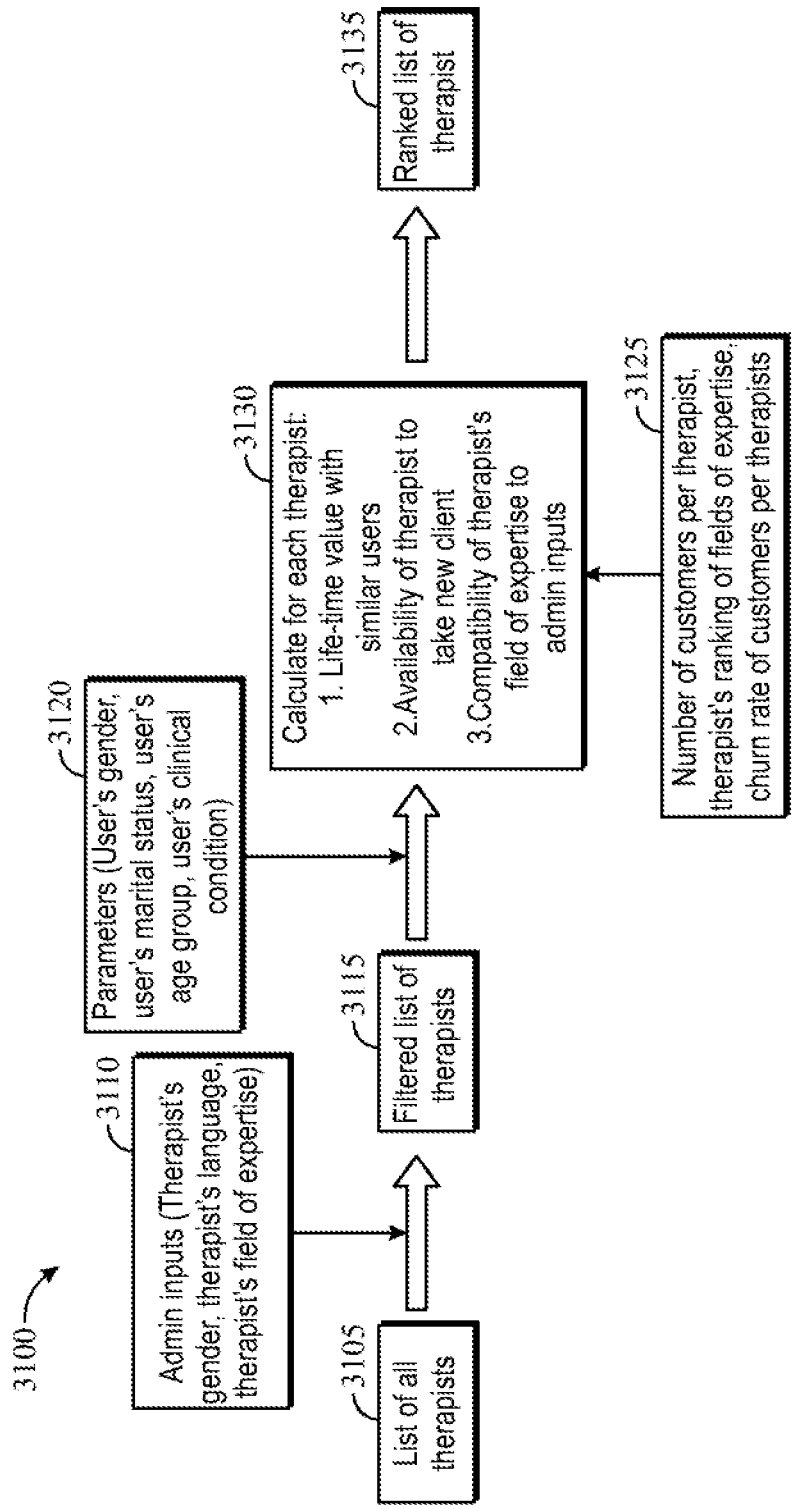
FIG. 31 shows a flow diagram of a process for matching clients and providers according to some embodiments.

With reference to FIG. 31, an exemplary process is shown according to some embodiments. The process operates on a list of providers (e.g., therapists) 3105. Based on provider information 3110 (e.g., the provider's gender, the provider's language, the provider's field of expertise), the list of providers is filtered (step 3115) to a subset of providers (e.g., subset of therapists). The providers may be filtered, in some embodiments, to a subset of providers which match a user's preferences of provider characteristics.

At 3120, a user's information (e.g., user's gender, marital status, age group, medical condition, etc.) may be obtained. At 3130, the system may predict how successful each of the filtered list of providers is likely to be with the given user. The prediction for each provider may be based on how the therapist has fared with prior clients with similar characteristics. Prior success may be measured in terms of duration of the prior client/provider relationship, the revenue obtained from the prior client, the prior client's improvement (e.g., in terms of medical condition), or in terms of any other factor.

The prediction 3130 may also take into account other considerations 3125, such as the number of customers each provider has seen (or is currently seeing), the way the provider has ranked his/her own areas of expertise, the rate at which the provide has lost customers in the past, and so on.

The predictions generated at 3130, once done for all providers from the filtered list 3115, may lead to a ranked list of providers (e.g., therapists) 3135 based on suitability of match for a given client.

Various embodiments include an algorithmic method for finding the best therapist for a given user based on the user's attributes and historical data of the therapist interacting with similar users.

Measuring Treatment

Various embodiments include determining scores for providers (e.g., for psychotherapists). Various embodiments include measuring success of services provided (e.g., of psychotherapy treatment) using an online platform.

Various embodiments include determining measurements used to score and rank providers (e.g., psychotherapists). In various embodiments, these measurements are based on past provider (e.g., therapist) engagement with customers. In various embodiments, these measurements allow for better matching between a customer and a provider (e.g., a therapist) and for improvement of the service (e.g., therapy) itself.

Where services (e.g., psychotherapy) are provided online, there is the possibility of gathering and using large amounts of data, e.g., provider-customer data, e.g., therapist-customer data, e.g., therapist-customer engagement data, in order to better assess (e.g., score; e.g., rank) how well the provider (e.g., therapist) was with his/her clients. In various embodiments, the assessment may involve customer feedback. In various embodiments, where assessments are given to providers (e.g., therapists) there is the possibility of building a better service (e.g., psychotherapy service) ecosystem by better matching between customers and providers (e.g., therapists) and also filtering out sub-performing providers (e.g., therapists).

In traditional scenarios where services (e.g., therapy) is provided face-to-face, relatively little data about the client-provider engagement or interaction may be recorded). In contrast, a system according to various embodiments serves as a platform via which the engagement between the two sides is conducted. Having the engagement facilitated by the platform enables using the potentially large amount of data generated in order to score the providers (e.g., therapists) and filter-out certain providers (e.g., sub-performing providers). Overall this may allow for a more stable and/or high-quality-of-service system.

A system according to various embodiments takes into account (e.g., utilizes as part of an assessment) one or more parameters: customer churn, e.g., how frequently customers left a particular provider (e.g., a particular therapist), how many messages were passed between the two sides, and how long the messages were. The system may also make use of customer ratings (e.g., customer ratings of providers), other providers' (e.g., therapists') rating of a given provider (e.g., a given therapist) and the particular customer's changing performance on all sorts of clinical assessment provided by the platform.

In various embodiments, because provider evaluations (e.g., scores) may be based on provider experiences with other users similar to a user of interest, a provider may receive differing evaluations with respect to two different prospective clients. For example, a provider may have had good results with clients in the age range of 30-45, but had only moderate results with client in the age range of 45-60. Accordingly, the same provider may receive different evaluations depending on whether a prospective client is 37 years old versus a prospective client who is 52 years old. In various embodiments, where a provider evaluation includes feedback from other providers, the provider evaluation may benefit from more inputs and more diverse inputs when compared to evaluations that are based on user feedback alone.

Various embodiments include a provider (e.g., psychotherapist) scoring system based on multiple inputs including other providers' (e.g., therapists') ratings, a customer's feedback, the customer's engagement, the provider's engagement, and clinical questionnaires filled out by the customer.

Determining Times for Providers to Reply

Various embodiments include a computer-implemented method comprising tracking of one or more actions (e.g., patient actions) carried out on a web-based computing platform (or any other platform) that enables text, audio, video and/or any other communication between providers (e.g., healthcare providers, e.g., behavioral healthcare providers) and their patients, determining a time by which the provider is expected to respond to the patient action, and alerting the provider of the expected response time, with a series of escalating alerts as the targeted time draws closer. In various embodiments, the actual time at which the provider responds may be compared to the targeted time and the patient presented with one or more actions he may take in the event the targeted time(s) is/are missed over the course of a set "weekly" period of available provider time (e.g. receive a free service, change providers). In various embodiments, the calculation of the response time target may be based on an underlying machine learning model. In various embodiments, the provider compensation may be automatically calculated to align with an amount credited to the patient if the provider fails to satisfy the specified service response time.

In various embodiments, patient engagement in asynchronous messaging-based behavioral health care may be encouraged when a provider makes timely replies to messages sent by his patient. However, because interactions between a patient and his provider are asynchronous, it is difficult to pre-determine a time frame within which providers are reasonably expected by the patient to respond to a patient message. A patient may send a sequence of messages that are meant to be considered in their entirety in order for the provider to have complete context. However, the entire sequence may span a time frame of 30-60 minutes, for example, due to the patient's need to identify and carefully express his thoughts. In another example, a patient may send a message to his provider that is simply a pleasantry, not requiring a response, for example "Good night." A system in which a provider is expected to always respond to a patient message within e.g. one hour, may unnecessarily introduce rigidity into patterns of interaction that are in fact more fluid and can vary greatly from one patient to another or from one day to the next for the same patient. On the other hand, failure to adequately set clear expectations for timeliness of a provider's response and/or allow the patient to immediately choose how they would like to be compensated for multiple missed response time deadlines can lead to patient dissatisfaction, resulting in low engagement and possible cancellation of the service.

In various embodiments, avoiding rigid response deadlines for providers may have one or more benefits, the benefits possibly including:

1. Ability to capture contextual information that can be used to determine if a patient message requires a timely response, e.g., within 2 hours, or can be responded to at some later time as is most convenient for the provider.
2. Ability to alert a provider in a variety of formats and to vary the alerts as the target time draws closer so as to maximize the likelihood that the provider will meet the service level expectations.
3. Ability to offer one or more alternatives for the missed provider response at the time the service level target is missed.

Figure 32:
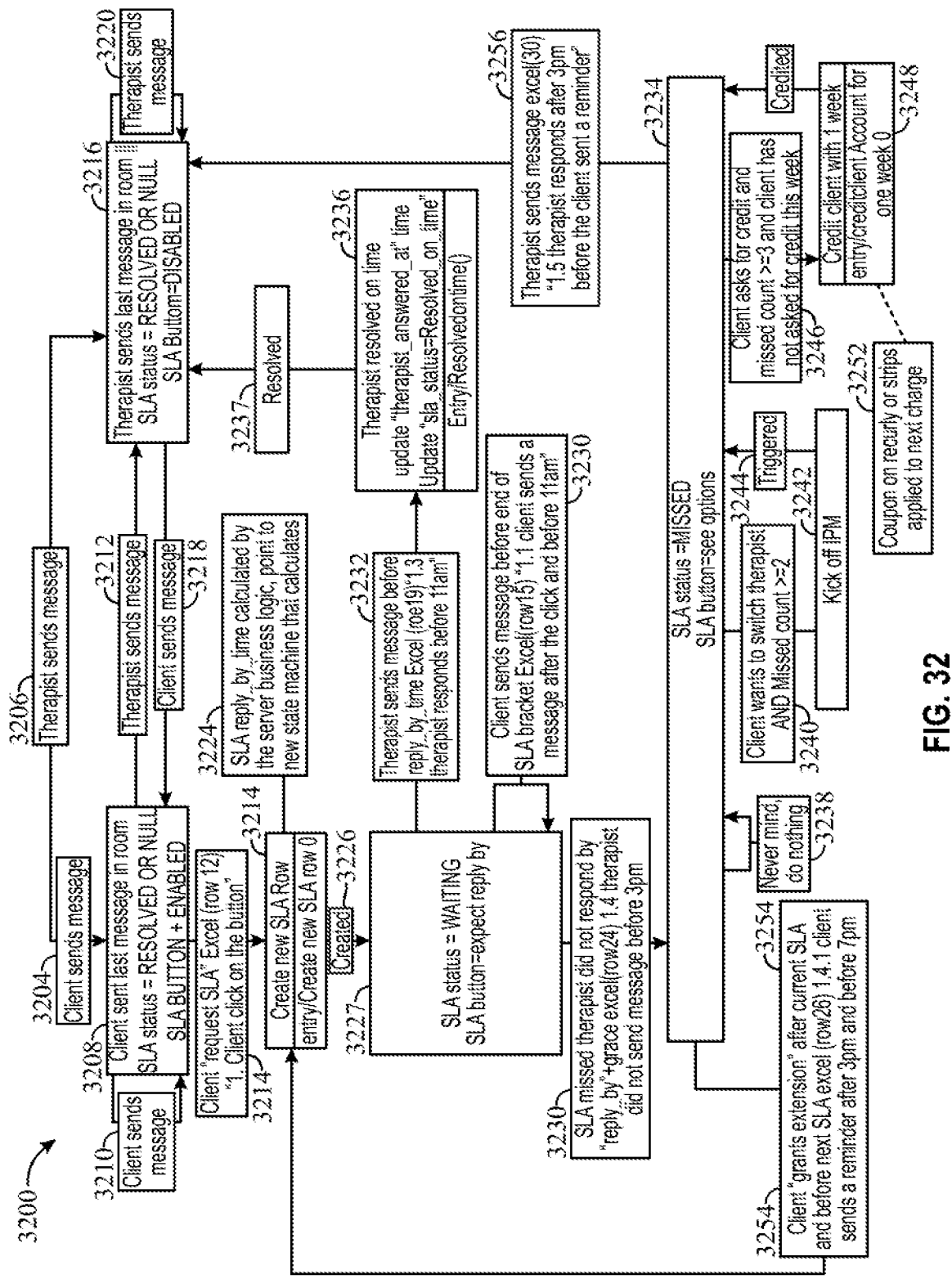
FIG. 32 shows a flow diagram of a process for facilitating providers to meet service obligations according to some embodiments.
Figure 33:
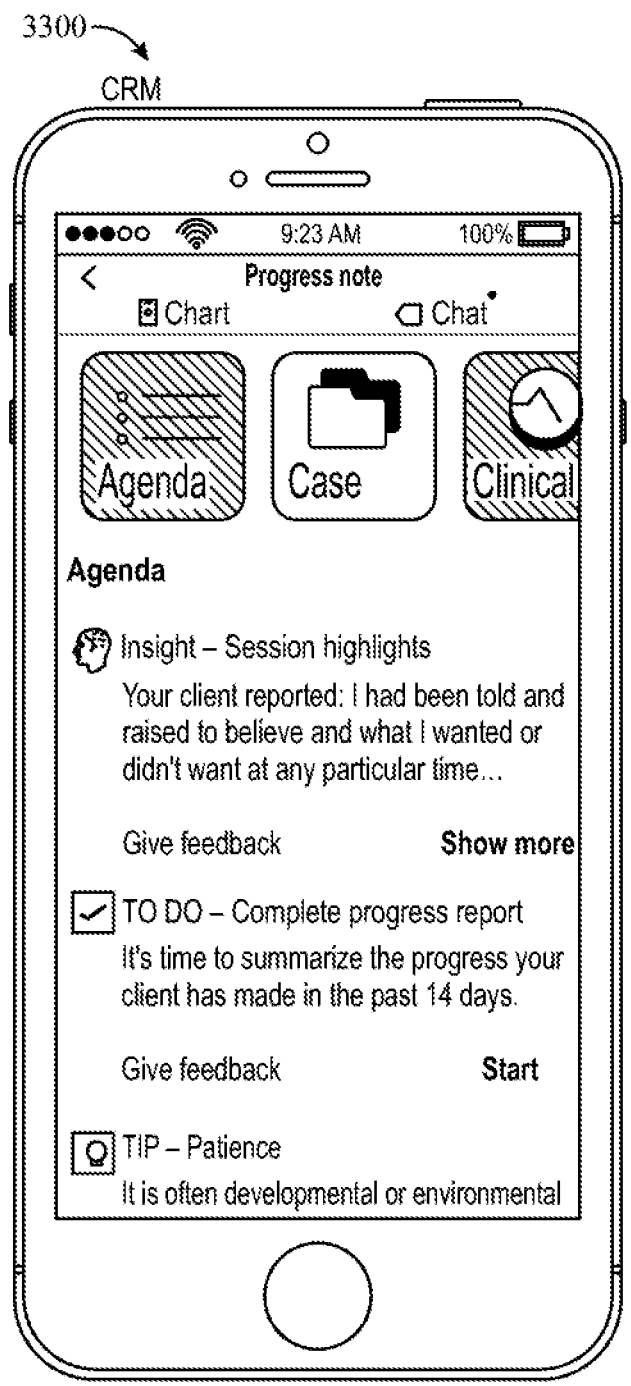
FIG. 33 shows a graphical interface according to some embodiments.
Figure 34:
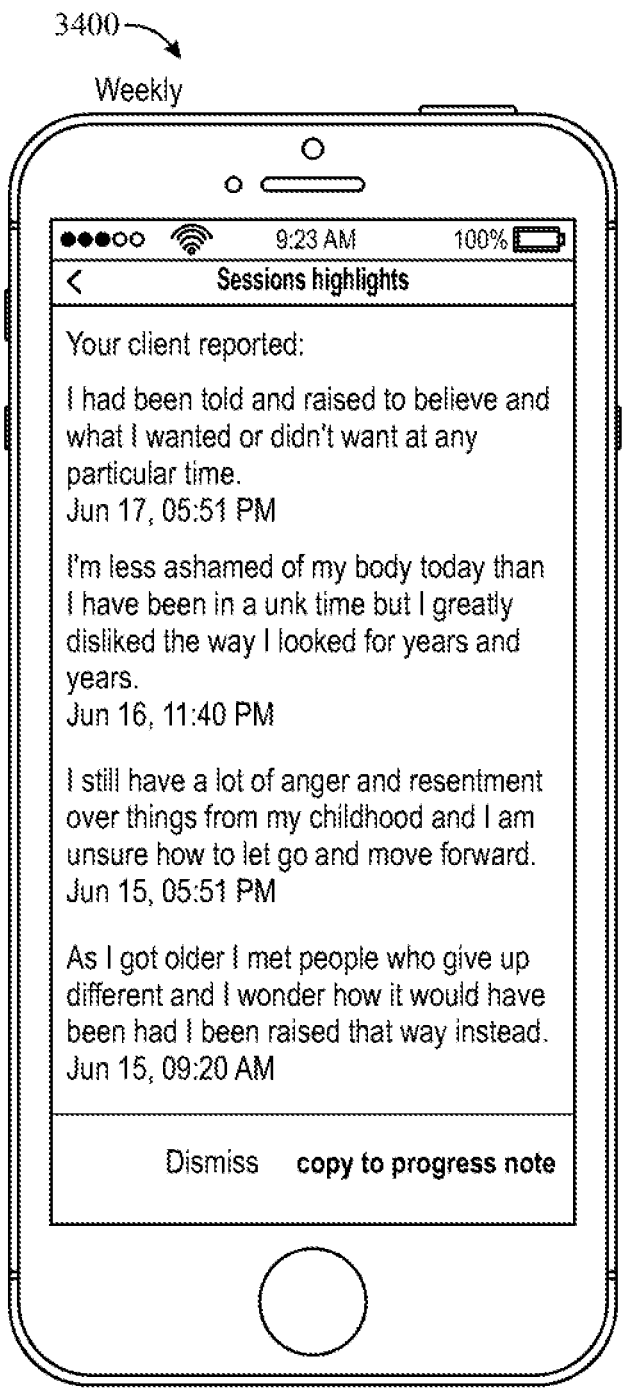
FIG. 34 shows a graphical interface according to some embodiments.
Figure 35:
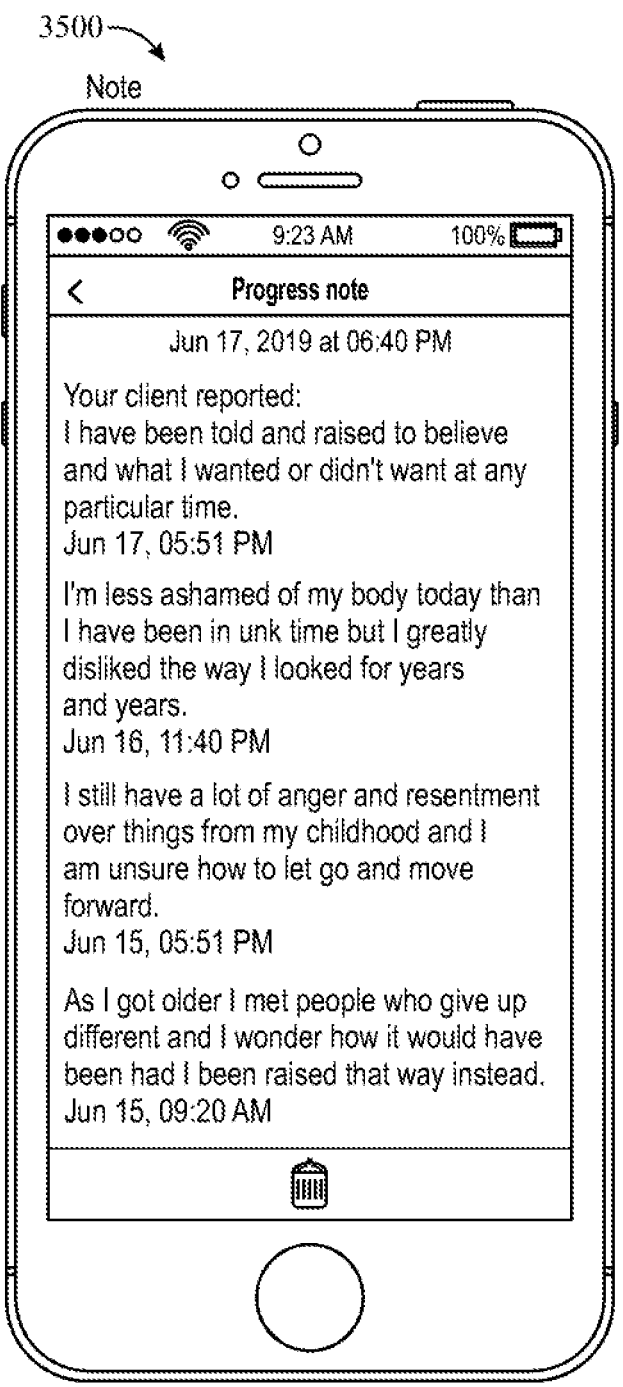
FIG. 35 shows a graphical interface according to some embodiments.
Figure 36:
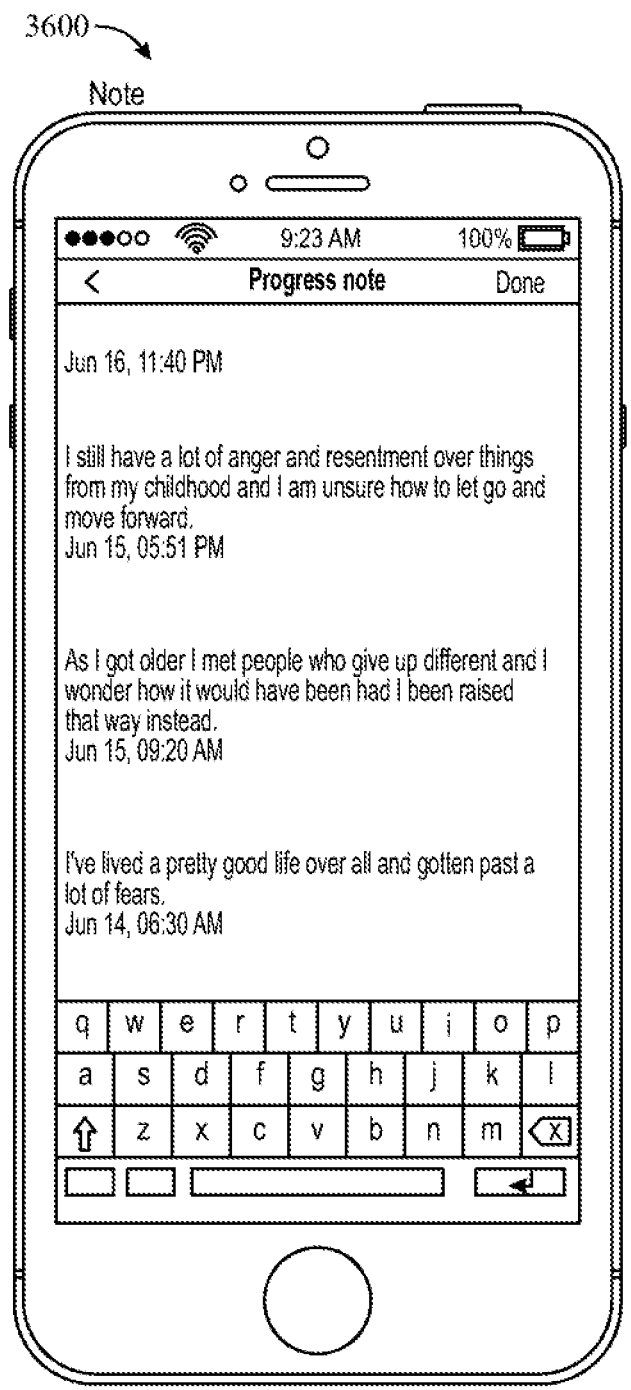
FIG. 36 shows a graphical interface according to some embodiments.

With reference to FIG. 32, there is illustrated a flow 3200 of information among components in a system that implements a process for determining a time for a provider to reply, and noting whether the provider did in fact reply in time, according to various embodiments.

In various embodiments, certain effects or outcomes may result from flow 3200. One outcome includes allowing a client to request a reply from a provider by a certain time by "enabling" an "SLA" button. In the event that a client does request the reply, another outcome is to actually now require the provider to send the reply by a certain deadline, to alert the client when the reply can be expected by, and to alert the provider as to when the reply is due. A third outcome is to record whether or not the provider successfully sent the reply in time. A fourth outcome is to redress the client's grievances if a timely reply has not been made some number of times.

Starting at 3202 or 3216 or 3208, the client may send a message. Flow then proceeds to block 3208, where an "SLA Button" is enabled. The "SLA Button" may appear as a button or other input area on the client's device and may be labeled "Request SLA" or the like. The client can now (step 3214) press the button to request a reply to his most recent message. (If, on the other hand, the provider already replies (step 3212) before the client even requests the reply, the flow proceeds to 3216, and the client now has no opportunity to request a reply). At 3222, a new row is created in a reply table (not shown), and may indicate the client, the provider, the deadline by which a reply is due, and whether or not the reply was made in time (though this last field may initially be empty).

In various embodiments, data structure 2600, may also indicate the client's room, the provider, and the deadline for the provider to reply.

At 3227, the client's graphical interface will now show that the client is waiting for a reply. In various embodiments, the client's interface shows the time remaining until a reply is to be expected.

If the therapist does in fact reply before the deadline 3232, flow proceeds to 3236, and the reply table, not shown, may be updated to reflect that the deadline was met successfully. The client's interface now no longer shows a time remaining to expect a reply, and there is no opportunity to request a new reply either.

Returning to 3227, a client may send any number of messages 3228 while waiting for the therapist to reply, and the provider's obligation to reply does not change.

If the provider fails to reply in time 3230, flow proceeds to 3234. The reply by table may be updated to indicate that the provider missed the deadline. The client's graphical interface may now present the client with a "See Options" button or other means to view options for redressing the provider's failure to reply in time.

For one, the client may grant an extension to the provider 3254, in which case flow returns to 3222. The client may choose to do nothing 3238. The client may choose to switch providers 3240, and the provider may even risk some privileges (e.g., ability to obtain new clients, etc.) at 3242. In various embodiments, the client may ask for some compensation 3246. In various embodiments, the client may ask for compensation only if the provider has missed some predetermined number of deadlines in the past week (e.g., 3). The client may receive the compensation at 3248, and compensation may include a coupon or discount applied to the next charge 3252.

Though the provider missed the deadline, the provider may eventually send a message 3256, in which case flow may proceed once again to 3216.

Summarization of Interactions

Various embodiments include a system and method for auto-generating summaries of messaging-based interactions between patients and healthcare providers.

Various embodiments include a computer-implemented method of auto-generating a clinical progress note comprising natural language analysis of the communication between providers (e.g., healthcare providers, e.g., behavioral healthcare providers) and their patients carried out on a web-based computing platform (or any other platform) that enables text, audio, video and/or any other form of communication and using the results of the analysis to create a written summary of the communication's content. In various embodiments, the provider may be alerted when the progress note has been auto-generated.

Progress notes documenting key aspects of a client's case, such as their current mental status and a recap of recent discussions, provide a way for a therapist to quickly and accurately recall aspects of a client's treatment, and are essential for effectively tracking treatment and collaborating with a treatment team. Even though asynchronous messaging-based behavioral health care may provide a record of some or all interactions between a client and his provider through the messaging history, the volume of messages exchanged in a given time frame, e.g. over the course of an entire week, may make it burdensome for a therapist to refer back to the messaging history and draw out highlights regarding the client's experience of symptoms and challenges for the purpose of writing a progress note. Providers working on a digital behavioral health platform may have caseloads larger than they might have in face-to-face practice; remembering important details in order to summarize each client's case may be mentally taxing and could require manually reviewing a large amount of text from the transcripts.

Additionally, the provider may want to provide observations regarding the mood and affect of the client as well, which will again require careful re-reading of the messages exchanged and their context, e.g. time of day the message was written.

Conventional systems for capturing progress notes disadvantageously require a provider to manually review and summarize the progress exhibited by the client in the course of the treatment. Additionally, the provider must decide when a progress note is warranted and remember to create the note.

Various embodiments may address these deficits through (a) determining when a progress note is warranted, based on, for example, the number of messages exchanged between the client and the provider or based on the time elapsed since creation of the previous progress note; (b) using Natural Language Understanding (NLU) techniques, such as general or domain-specific word embeddings in combination with machine learning approaches, such as cluster analysis, to auto-generate a summary of the key elements of the messaging interactions; (c) alerting the provider as to when a progress note has been auto-generated and providing a link to the auto-generated note that opens the note in 'draft' mode for further editing. Various embodiments describe how such a process can be implemented within the context of a web-based computing platform that enables text, audio, and/or video-based communication between behavioral healthcare providers and their patients. However, it will be appreciated that various embodiments contemplate the implementation approach described herein in other domains (e.g., in domains besides healthcare, behavioral health etc.), and on other platforms.

Exemplary Methodology for Auto-Creation of Draft Progress Note

In various embodiments, the method for creating the progress note content exploits a characteristic feature of psychotherapy transcripts: important descriptions of the client's presentation often appear as first-person statements made by the client, e.g., "I have been so anxious this week." This heuristic is also useful because statements like this tend to be more self-contained and interpretable when read as excerpts. In this exemplary method, both client and therapist statements are used to identify the important topics of the transcript and these measures of importance are used to rank and return the most important first-person client statements. The steps involved in this exemplary method are as follows:
1. Normalize text and break into a sequence of sentences, which may represent only a part of a message.
2. Compute the similarity between each pair of sentences.
    a. Convert each sentence to a collection of lemmatized n-grams where n ranges between 1 and 6 (inclusive).
        i. Keep only n-grams that do not start or end with a stop word and do not contain punctuation.
    b. Convert each sentence to a vector using, for example, a topic frequency-inverse document frequency (tfidf)-based metric, where each term weight is calculated as:

$$\frac{tf * (k+1)}{tf + k * (1 - b + b * (\text{length}/avg(\text{lengths})))} * \log\left(\frac{n_{docs}+1}{df+1}\right) + 1 \text{ and } k = 1.6 \text{ and } b = 0.75$$

are commonly used parameters for this transformation.
    c. Define the similarity between a pair of sentences as the cosine similarity between their tfidf vectors.
3. Build a term co-occurrence graph
    a. For each pair of terms from step 2a, the edge weight between them is the sum of the similarities of all sentence pairs in which they both occur. Using the sentence tfidf similarities means that term co-occurrence weights are greater when two terms tend to appear in similar contexts. The weights are lower when two terms tend to appear in dissimilar or random contexts.
4. Score the importance of each term using the eigenvector centrality of its corresponding node in the term co-occurrence graph. Roughly, this can be interpreted as the amount of time you would spend reading each term if you read the transcript by jumping from term to term based on how similar their contexts are. This process should result in "circling around" groups of interrelated terms corresponding to topics.
5. For each client sentence, extract sentence fragments where the client is saying something in the first person. (e.g. "I've been doing better this week."), using, for example, a method such as that described in step 1.
6. Score each extracted sentence fragment generated in step 5 by summing the term scores calculated in step 4 for each term in the fragment (taking care not to multiple-count the constituent words of n-grams where n>1) and dividing by the square root of the number of words in the fragment.
    a. Full sentences are also scored and allowed to be included in the results if they include a first-person client statement and have a higher (length-normalized) score than any fragments extracted from them.
    b. All candidate extracts (fragments or full sentences) are excluded if they exceed n words in length, where n is chosen to appropriately balance trade-off between importance and summarization.
7. Extract the highest-scoring first-person client statements and return them in the order in which they originally appear in the transcript, where highest-scoring is selected based on clinical objectives.

Note that in various embodiments, the method used to compute similarity in Step 2 can be based on a different similarity metric and different approach to vectorizing the text of each sentence.

In various embodiments, the creation of the draft progress note might be triggered every seven days, with a notification surfaced to the provider within a dashboard showing the specific client's clinical information. An exemplary embodiment might show a preview of the draft progress note within a Session Highlights agenda card, such as depicted in FIGS. 33-36. If the therapist clicks "Show more" they are taken to a new window where they can view the complete highlights. This window might also contain some kind of header text with an explanation to the provider for how to use the highlights to write a progress note. Then they can select "Copy to progress note" to create a new note containing the highlights which they can then edit.

Figure 37:
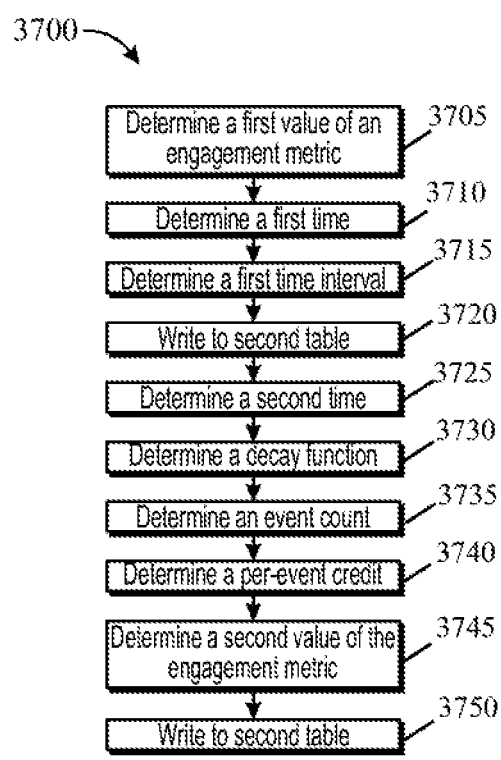
FIG. 37 shows a flow diagram of a process according to some embodiments.

With reference to FIG. 37, in step 3705 the system may work with a first table, e.g., table 2100 in FIG. 21, and a second table, e.g., table 2400 in FIG. 24, and may determine a first value of an engagement metric. In non-limiting examples, this may be S_0 (value 1) as described in connection with 2710 in FIG. 27, or may be a Score Immediately After Event 2135 described in connection with FIG. 21, e.g., 1.58 in row 2. In step 3710, the system may determine a first time associated with the first value of the engagement metric. This may be Event Time 2110 of FIG. 21, e.g., Jan. 12, 2023 11:00 AM in row 2. In step 3715, the system may determine a first time interval. In various aspects, this may be time passed described at 2730 in connection with FIG. 27; may be the time between 'Hourly Snapshot' entries in Event Type 2115 of FIG. 21, (1 hour); and may be time between columns Hour_0_score 2420 and Hour_1_score 2425 in FIG. 24.

In step 3720, the system may write the first time and the first value to the second table, which may be table 2400. In some instances, the first value is written and the first time is not entered or is automatically entered or inferred based on the first time. In step 3725, the system may determine the second time as the first time plus the first time interval. This may be the next 'Hourly Snapshot' entry in Event Type 2115 of FIG. 21, which is Jan. 12, 2023 12:00 PM (row 4). In step 3730, the system may determine a decay function that is a function of an elapsed time interval. One such function is described in detail in connection with FIG. 27, above. In step 3735, the system may determine an event count by performing an aggregating function encompassing events between the first and second times. This may be achieved by counting the number of events between Hourly Snapshots in Event Type 2115 in FIG. 21. For example, between Jan. 12, 2023 3:00 PM (row 7) and Jan. 12, 2023 4:00 PM (row 10) there were two Messages, so the event count would be 2 for this interval of time. In step 3740, the system may determine a per-event credit, such as S_i, as described in connection with step 2710 in FIG. 27.

In step 3745, the system may determine a second value of the engagement metric. To do this, the system may compute a first product by multiplying (a) the first value of the engagement metric; by (b) a value of the decay function computed with the elapsed time interval set equal to the first time interval. It will be understood this is the mathematical equivalent of the steps performed in step 2740 in FIG. 27. The system may then compute a second product by multiplying the event count and the per-event credit. This may be computed similarly to the index increase (S_i times the number of messages) described in steps 2750 and 2760 of FIG. 27. The system may then sum the first product and the second product (increase index by S_i) as described in step 2760.

Finally, in step 3745, the system may write the second time and the second value to the second table. For example, the second value may be Hour_1_score 2425 in FIG. 24.

The foregoing has described various embodiments, but it will be understood that contemplated embodiments are not limited only to what has been explicitly described herein.

Applicants claim:

1. A method for providing information to a database measuring consumer engagement with providers, the database having a first table storing times of occurrence for one or more events and a second table storing values of an engagement metric, the information provided via a processor operable to execute computer instructions comprising:
   determining a first value of an engagement metric;
   determining a first time associated with the first value of the engagement metric;
   determining a first time interval representing a time difference between a second time with which a second value of the engagement metric is associated and the first time;
   writing the first time and the first value to the second table;
   determining the second time as the first time plus the first time interval;
   determining a decay function that is a function of an elapsed time interval;
   determining an event count by performing an aggregating function on the first table, where the aggregating function encompasses events with times of occurrence between the first time and the second time;
   determining a per-event credit;
   determining a second value of the engagement metric by:
      i. computing a first product by multiplying the first value of the engagement metric and a value of the decay function computed with the elapsed time interval set equal to the first time interval;
      ii. computing a second product by multiplying the event count and the per-event credit;
      iii. summing the first product and the second product; and
   writing the second time and the second value to the second table.

2. The method of claim 1, wherein the one or more events include the transmission of a text message from a consumer to a provider.

3. The method of claim 1, wherein the first value of the engagement metric is 1.

4. The method of claim 1, wherein the decay function is an exponential function of time.

5. The method of claim 1, wherein the aggregating function is a database aggregating function.

6. The method of claim 1, wherein the aggregating function is a 'COUNT' function used in conjunction with a 'GROUP BY' aggregation.

7. The method of claim 1, preventing a provider from executing an action when a time to complete a task exceeds a predetermined threshold.

* * * * *